(12) United States Patent
Ney et al.

(10) Patent No.: US 9,180,168 B2
(45) Date of Patent: Nov. 10, 2015

(54) USE OF GLYCOMACROPEPTIDE TO IMPROVE WOMEN'S HEALTH

(71) Applicant: Wisconsin Alumni Research Foundation, Madison, WI (US)

(72) Inventors: Denise M. Ney, Brooklyn, WI (US); Eric Chi-Liang Yen, Madison, WI (US); David W. Nelson, Madison, WI (US); Patrick Solverson, Viroqua, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/755,893

(22) Filed: Jan. 31, 2013

(65) Prior Publication Data

US 2013/0196905 A1    Aug. 1, 2013

Related U.S. Application Data

(60) Provisional application No. 61/593,157, filed on Jan. 31, 2012, provisional application No. 61/672,555, filed on Jul. 17, 2012.

(51) Int. Cl.
*A61K 38/22* (2006.01)
*A23L 1/305* (2006.01)
*A61K 38/01* (2006.01)
*A61K 38/17* (2006.01)

(52) U.S. Cl.
CPC .............. *A61K 38/22* (2013.01); *A23L 1/3053* (2013.01); *A61K 38/018* (2013.01); *A61K 38/1709* (2013.01); *A23V 2002/00* (2013.01)

(58) Field of Classification Search
None
See application file for complete search history.

(56) References Cited

U.S. PATENT DOCUMENTS

2004/0052860 A1*  3/2004  Reid et al. ...................... 424/535
2007/0128252 A1*  6/2007  Ward et al. ..................... 424/439
2010/0317597 A1* 12/2010  Ney et al. ...................... 514/20.9

FOREIGN PATENT DOCUMENTS

WO    WO 00/49885    *  8/2000

OTHER PUBLICATIONS

Solverson et al "Glycomacropeptide, a low-phenylalanine protein isolated from cheese whey, supports growth and attenuates metabolic stress in the murine model of phenylketonuria" (Jan. 31, 2012) Am J Physiol Endocrinol Metab 302: E8885-E895).*
Weyer et al ("Energy Expenditure, Fat Oxidation, and Body Weight Regulation: A Study of Metabolic Adaptation to Long-Term Weight Change" (2000) J Clin Endocrinol Metab 85(3): 1087-1094).*
Woo (Ann Intern Med (2006) 144: 753-761).*
Mokdad et al (JAMA (2003) 289(1):76-79).*
Weyer et al (J Clin Endocrinol Metab (2000) 85(3): 1087-1094).*
Brody, Biological Activities of Bovine Glycomacropeptide, British Journal of Nutrition, 2000, 84(Supp 1):S39-S46.
Burton-Freeman, Glycomacropeptide (GMP) is Not Critical to Whey-Induced Satiety, But May Have a Unique Role in Energy Intake Regulation Through Cholecystokinin (CCK), Physiology & Behavior, 2008, 93(1-2):379-387.
De Groot, et al., Relationships Between Lumbar Bone Mineral Density and Biochemical Parameters in Phenylketonuria Patients, Molecular Genetics and Metabolism, 2012, 105(4):566-570.
Lam, et al., The Influence of Whey Protein and Glycomacropeptide on Satiety in Adult Humans, Physiology & Behavior, 2009, 96(1):162-168.
MacLeod, et al., Breakfast with Glycomacropeptide Compared with Amino Acids Suppresses Plasma Ghrelin Levels in Individuals with Phenylketonuria, Molecular Genetics and Metabolism, 2010, 100(4):303-308.
McDonald, et al., Pah(hph-5): A Mouse Mutant Deficient in Phenylalanine Hydroxylase, Proc. Natl. Acad. Sci. USA, 1990, 87:1965-1967.
Nagasaka, et al., Cross-Sectional Study of Bone Metabolism with Nutrition in Adult Classical Phenylketonuric Patients Diagnosed by Neonatal Screening, J. Bone Miner. Metab., 2011, 29:737-743.
Ney, et al., Dietary Glycomacropeptide Supports Growth and Reduces the Concentrations of Phenylalanine in Plasma and Brain in a Murine Model of Phenylketonuria, Journal of Nutrition, 2008, 138:316-322.
Perez-Duenas, et al., New Approach to Osteopenia in Phenylketonuric Patients, Acta Paediatrica, 2002, 91 (8):899-904.
Roato, et al., Bone Impairment in Phenylketonuria is Characterized by Circulating Osteoclast Precursors and Activated T Cell Increase, PLoS One, 2010, 5(11):e14167, 9 pages.
Solverson, et al., Glycomacropeptide, A Low-Phenylalanine Protein Isolated from Cheese Whey, Supports Growth and Attenuates Metabolic Stress in the Murine Model of Phenylketonuria, Am. J. Physiol. Endocrinol. Metab., 2012, 302: E885-895.

(Continued)

Primary Examiner — Karlheinz R Skowronek
Assistant Examiner — Mindy Newman
(74) Attorney, Agent, or Firm — Quarles & Brady LLP

(57) ABSTRACT

Methods for improving the health of a female human or non-human animal are disclosed. The methods include the step of administering to the animal compositions including an effective amount of glycomacropeptide (GMP) for effectuating the methods. Specifically, the methods can be used to increase the rate of fat metabolism or fat oxidation, decrease percentage of body fat, increase the rate of bone mineralization, increase bone mineral content, increase bone mineral density, and/or increase bone strength in the animal.

GMP-containing compositions can be used according to the disclosed methods to treat obesity and related metabolic conditions, or to treat or prevent osteoporosis, osteopenia, and other conditions related to loss of bone mineral content or bone strength.

8 Claims, 20 Drawing Sheets

(56) References Cited

OTHER PUBLICATIONS

Solverson, et al., Low Bone Strength Is A Manifestation of Phenylketonuria in Mice and Is Attenuated by a Glycomacropeptide Diet, PLoS ONE, 2012, 7(9):e45165, 12 pages.

Veldhorst, et al., Effects of Complete Whey-Protein Breakfasts Versus Whey Without GMP Breakfasts on Energy Intake and Satiety, Appetite, 2009, 52(2):388-395.

Van Calcar, et al., Improved Nutritional Management of Phenylketonuria by Using a Diet Containing Glycomacropeptide Compared with Amino Acids, Am. J. Clin. Nutr., 2009, 89:1068-1077.

Van Calcar, et al., Food Products Made with Glycomacropeptide, A Low-Phenylalanine Whey Protein, Provide a New Alternative to Amino Acid-Based Medical Foods for Nutrition Management of Phenylketonuria, J. Acad. Nutr. Diet., 2012, 112:1201-1210.

Yannicelli, et al., Elevated Plasma Phenylalanine Concentrations May Adversely Affect Bone Status of Phenylketonuric Mice, J. Inherit. Metab. Dis., 2002, 25:347-361.

* cited by examiner

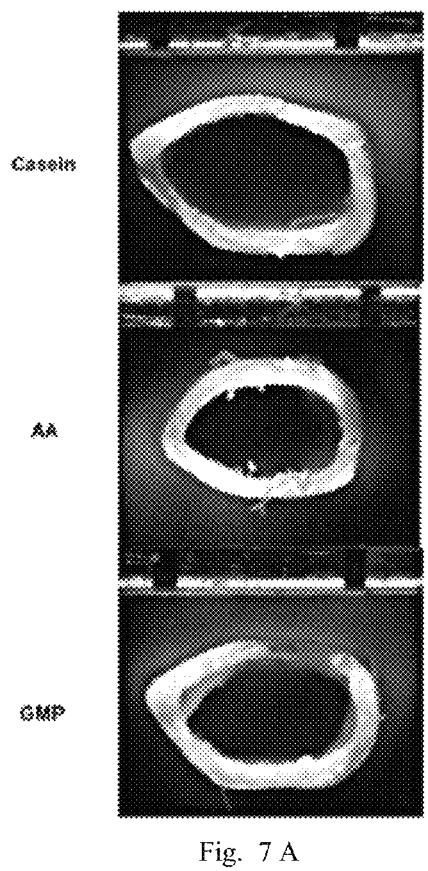
Fig. 7 A
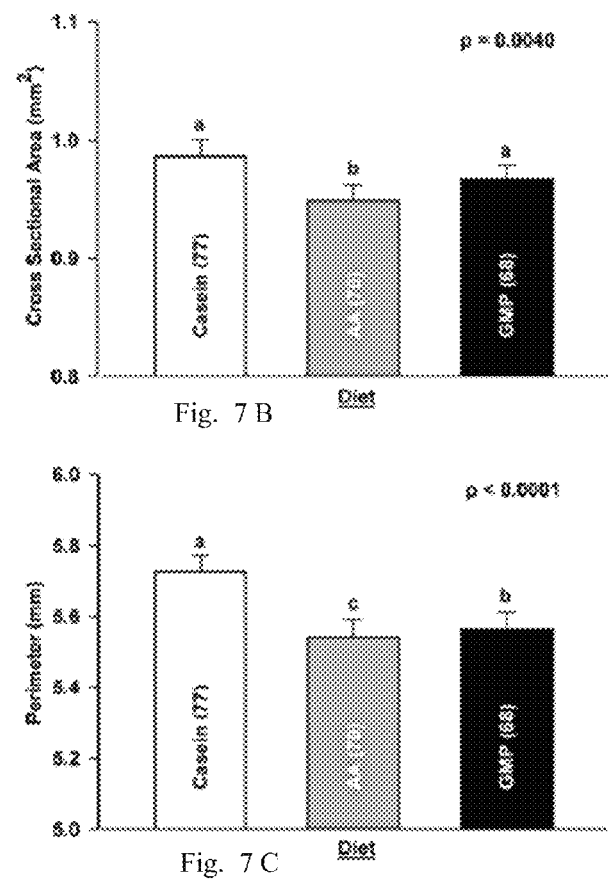
Fig. 7 B
Fig. 7 C

USE OF GLYCOMACROPEPTIDE TO IMPROVE WOMEN'S HEALTH

CROSS-REFERENCE TO RELATED APPLICATION

This application claims the benefit of U.S. Provisional Application No. 61/593,157, filed on Jan. 31, 2012, and of U.S. Provisional Patent Application No. 61/672,555, filed on Jul. 17, 2012, both of which are incorporated by reference herein.

STATEMENT REGARDING FEDERALLY SPONSORED RESEARCH OR DEVELOPMENT

This invention was made with government support under 11-CRHF-0-6055 awarded by the USDA/NIFA. The government has certain rights in the invention.

FIELD OF THE INVENTION

This disclosure relates generally to methods of improving women's health by administering to women nutraceuticals, dietary supplements, or foods containing glycomacropeptide (GMP). In particular, when administered to a female human or non-human animal, compositions containing GMP can be used to increase the rate of fat oxidation/metabolism, decrease percentage of body fat, increase the rate of bone mineralization, increase bone mineral content, increase bone mineral density, and/or increase bone strength.

BACKGROUND OF THE INVENTION

Human health can be negatively affected by factors such as increasing body fat or decreasing bone strength or bone mineralization.

For example, obesity is a medical condition in which excess body fat has accumulated to the extent that it may have an adverse effect on health. Obesity increases the risk of developing certain diseases, such as heart disease, type 2 diabetes, obstructive sleep apnea, certain types of cancer, and osteoarthritis. Obesity is a growing public health problem in the United States and throughout the world.

Dieting, behavior modification and physical exercise are the standard treatments for obesity. However, despite widespread awareness of the importance of diet and exercise, obesity is increasingly prevalent in both adults and children. Current alternative treatments for obesity include medications to reduce appetite or to inhibit fat absorption. In severe cases, surgery is performed to reduce stomach volume and/or bowel length, leading to earlier satiation and reduced ability to absorb nutrients from food.

Interventions aimed at increasing the rate of fat metabolism could potentially reduce the symptoms of obesity by facilitating the increased oxidation of excess fat, leading to a decreased percentage of body fat. However, the biochemical factors that may increase or decrease the rate of fat oxidation are not well-understood. Although physical exercise has been shown to increase the rate of fat metabolism, few foods or dietary supplements have been shown to effectively increase the rate of fat oxidation. Thus, there is a need in the art for foods, dietary supplements or nutraceutical that have the demonstrated ability to increase an individual's rate of fat metabolism/oxidation or to decrease the percentage of fat in an individual's body.

As a second example, mineralization of bone is the result of a complex process in which crystals of calcium phosphate are produced by bone-forming cells and laid down in precise amounts within the bone's fibrous matrix or scaffolding. Bone mineral loss is a well-known consequence of aging, and both men and women slowly lose bone mineral content and exhibit decreased bone mineral density beginning at age 30. Post-menopausal woman are at increased risk for additional loss of bone mineral content and decreased bone mineral density, most likely due to decreased estrogen levels.

Decreasing rates of bone mineralization, decreased bone mineral content, and decreased bone mineral density are associated with a wide variety of conditions, and may result in significant medical problems. For example, osteoporosis is a debilitating disease in humans characterized by marked decreases in skeletal bone mass and mineral density and corresponding increases in bone fragility and susceptibility to fracture in afflicted individuals. Fractured hips, wrists, and vertebrae are among the most common injuries associated with osteoporosis. Hip fractures in particular are extremely uncomfortable and expensive for the patient, and for women, correlate with high rates of mortality and morbidity. Osteoporosis is preceded by clinical osteopenia, a very common condition throughout the world. The frequency of osteopenia and osteoporosis increases with age, and they are much more common in women than in men.

Current strategies for the prevention of osteopenia, osteoporosis, and other conditions associated with bone mineral loss include physical activity with the onset of advanced age (specifically, weight bearing activity), preventing calcium deficiency through diet, and avoiding consumption of tobacco. For patients with clinical osteopenia or osteoporosis, most current therapeutic strategies are directed to reducing further loss of bone mass by inhibiting the process of bone resorption.

However, no foods or dietary supplements have been explicitly shown to effectively increase the rate of bone mineralization, or the mineral content or mineral density of bone. Thus, there is a need in the art for foods, dietary supplements or nutraceutical that have the demonstrated ability to increase an individual's bone mineral content or bone strength, particularly in women. Such compositions could be utilized to treat a wide variety of conditions, such as osteopenia, osteoporosis, increased susceptibility to fractures, and other disorders associated with decreased bone mineralization.

SUMMARY OF THE INVENTION

The inventors have surprisingly determined that administering glycomacropeptide (GMP) can improve the health of a female human or non-human animal. Specifically, administering a composition comprising GMP to a female animal can increase the rate of fat oxidation and fat metabolism and/or reduce the percentage of body fat in the animal, and increase bone mineralization, bone mineral content, bone mineral density, and/or bone strength in the animal. Surprisingly, these effects are much less significant or nonexistent in males.

This disclosure encompasses a method for improving the health of a female non-human or human animal. The method includes the step of administering an effective amount of a composition comprising glycomacropeptide (GMP) to the female animal, wherein the health of the animal is improved.

In certain embodiments, the composition is administered orally. Examples of GMP compositions that can be used in the method include, without limitation, a food product, a nutraceutical, or a dietary supplement.

In certain embodiments, the animal is a human.

In certain embodiments, the effective amount of the composition is such that from 0.15 to 1.0 g GMP per kg of body weight is administered to the animal per day.

The method is effective both in individuals having a metabolic disorder such as phenylketonuria (PKU) and in individuals unaffected by such disorders. Accordingly, in certain embodiments, the animal to which the composition is administered does not have phenylketonuria (PKU).

In certain embodiments, the method increases the rate of fat oxidation or fat metabolism in the female animal, reduces the percentage of body fat in the female animal, increases the rate of bone mineralization in the female animal, increases the bone mineral content or bone mineral density in the female animal, and/or increases bone strength in the female animal.

The method can be used to treat any condition associated with excess body fat or decreased fat metabolism. A non-limiting example of such a condition is obesity. The method can also be used to treat any condition associated with decreased bone mineralization or bone strength. Non-limiting examples include osteopenia and osteoporosis.

These and other features of the disclosed method will become apparent to the skilled artisan from the following detailed description considered in conjunction with the accompanying figures.

BRIEF DESCRIPTION OF THE DRAWINGS

FIG. 8 includes bar graphs showing bone mineralization data (BMC, top panel and BMD, bottom panel) for all mice (both wild type and PKU) separated into cohorts by sex (male/female) and diet (casein/amino acid/GMP). Female mice (both wild type and PKU) fed the GMP diet demonstrated significantly greater bone mineralization compared with female mice fed the casein diet. Sample size for each cohort is indicated in parenthesis. Mean values with different superscript letters are significantly different, p<0.05.

FIG. 9 includes bar graphs showing bone strength data (as measured by maximum strength before femoral fracture) for all mice (both wild type and PKU) separated into cohorts by sex (male/female) and diet (casein/amino acid/GMP). Female mice (both wild type and PKU) fed the GMP diet demonstrated significantly greater bone strength as compared with female mice fed the casein diet or the amino acid diet.

Figure 1A:
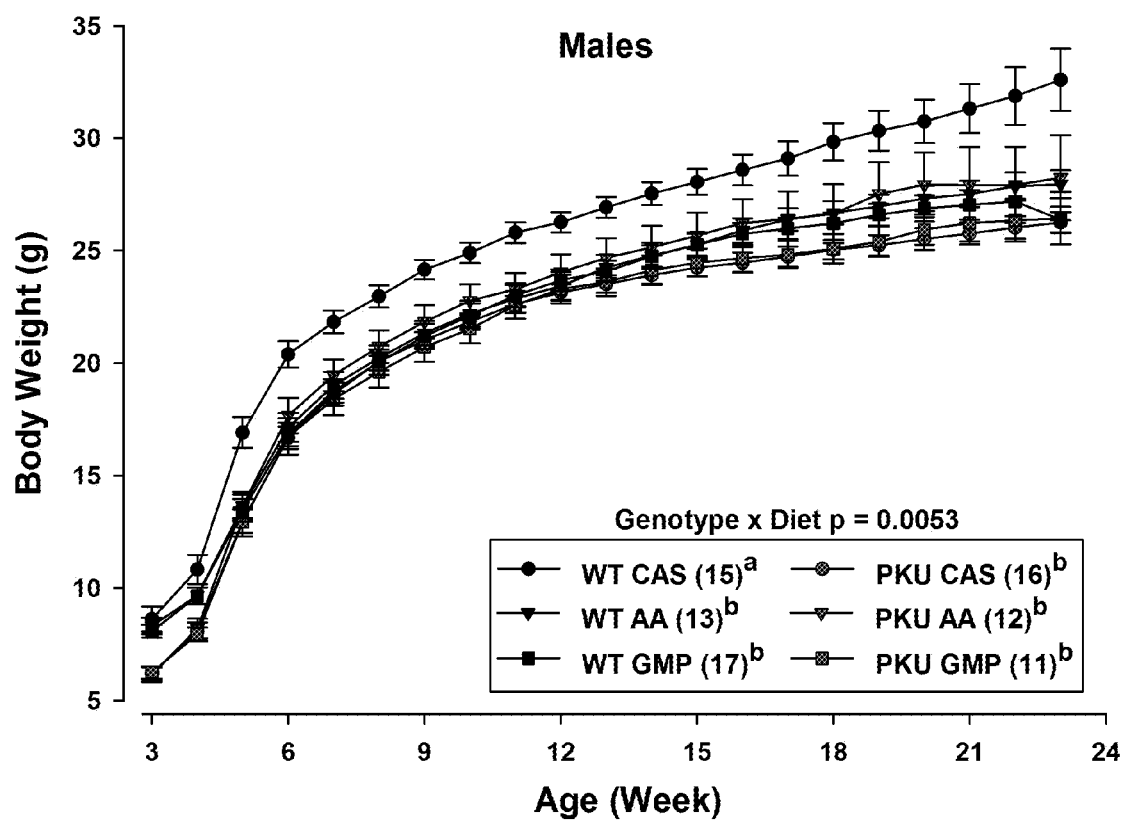
FIGS. 1A and 1B are graphs of body weight as a function of age showing the change in body weight of male (FIG. 1A) and female (FIG. 1B) PKU and WT mice fed casein, AA or GMP diets from weaning (3 wk) through 23 weeks of age. Repeated measures analysis indicated significant genotype x diet interaction for both male and female mice. Values are means±SE; means with different superscripts are significantly different (p<0.05) as shown in the legend along with the sample sizes noted in parentheses.

Sample size for each cohort is indicated in parenthesis. Mean values with different superscript letters are significantly different, p<0.05.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The following abbreviations are used throughout the present disclosure: AA, amino acid; Ala, alanine; Arg, arginine; Asn, asparagine; Asp, aspartic acid; BMC, bone mineral content; BMD, bone mineral density; Cys, cysteine; DXA, dual-energy x-ray absorptiometry; Gln, glutamine; Glu, glutamic acid; Gly, glycine; GMP, glycomacropeptide; His, histidine; Iso or Ile, isoleucine; Leu, leucine; Met, methionine; PAH, phenylalanine hydroxylase; PCR, polymerase chain reaction; Phe, phenylalanine; PKU, phenylketonuria; Pro, proline; RER, respiratory exchange ratio; SE, standard error (of the mean); Ser, serine; Thr, threonine; Tyr, tyrosine; Trp, tryptophan; Val, valine; WT, wild type.

II. The Invention

The inventors have recently demonstrated using a mouse model that orally administered compositions containing glycomacropeptide (GMP) can improve the health of female animals.

First, such compositions can increase the rate of fat metabolism/oxidation and can reduce body fat percentage. Previously, studies have demonstrated that GMP may promote satiety and modulate food intake in both control subjects (Brody, *Br J Nutr* 84 Suppl 1: S39-46, 2000; Lan et al., *Physiol Behav* 96: 162-168, 2009 (8, 26, 53); Veldhorst et al., *Appetite* 52: 388-395, 2009) and in subjects with PKU (Macleod et al., *Mol Genet Metab* 100(4): 303-308, 2010). This response has been linked with the ability of GMP to stimulate cholecystokinin release (Burton-Freeman, *Physiol Behav* 93: 379-387, 2008), inhibit ghrelin release after eating (Macleod et al., *Mol Genet Metab* 100(4): 303-308, 2010), and the high content of branched chain AA in GMP.

In this disclosure, we demonstrate for the first time that GMP compared with an AA diet significantly lowers the respiratory exchange ratio during the dark cycle in both WT and PKU mice, a result that is consistent with increased fat oxidation and supported by a significantly lower percentage of body fat in PKU mice fed GMP. Interestingly, female compared with male mice showed a more pronounced response to the GMP diet in lowering RER and percentage of body fat. Accordingly, the present disclosure provides methods of increasing fat metabolism/oxidation or reducing body fat percentage in a female human or non-human animal by administering to the animal a composition that includes GMP.

Second, such compositions can increase bone mineralization and bone strength in females. This increase is demonstrated by a statistically significant increase in measured bone mineral content (BMC) and bone mineral density (BMD) in female wild type and PKU mice as compared to mice fed a control casein diet, and by a statistically significant increase in bone strength in female wild type and PKU mice as compared to mice fed a control casein diet or an amino acid diet. Accordingly, the present disclosure provides methods of increasing bone mineralization, increasing bone mineral content, increasing bone density, and/or increasing bone strength in a female human or non-human animal by administering to the animal a composition that includes GMP.

GMP is a 64 AA glycophosphopeptide, corresponding to AA 106-169 of κ-casein, that is released in the human stomach after ingestion of bovine milk or yogurt (Chabance et al., *Biochimie* 80: 155-165, 1998). For commercial use, GMP is obtained from cheese making when κ-casein is cleaved by rennet chymosin into para-κ-casein, which remains with the cheese curd, and GMP, which remains with the whey (Etzel, *J Nutr* 134: 996S-1002S, 2004). GMP, the third most abundant protein in cheese whey, is highly polar with an isoelectric point below 3.8 and is glycosylated by galactosamine, galactose, and o-sialic acid at threonine sites (Laclair et al., *J Food Sci* 74: E199-206, 2009). Moreover, GMP has a unique AA profile including an absence of aromatic AA, phe, tryptophan and tyrosine, as well as arginine, cysteine and histidine, and concentrations of isoleucine and threonine that are 2-3 fold greater, respectively, than those found in other dietary proteins (Etzel, *J Nutr* 134: 996S-1002S, 2004). GMP supplemented with limiting AA provides a low-phe source of dietary protein that is an acceptable alternative to AA formula and can be made into an array of foods and beverages to enhance variety in the low-phe diet required for those with phenylketonuria (PKU) (Van Calcar et al., *Am J Clin Nutr* 89: 1068-1077, 2009; Van Calcar and Ney, J Acad Nutr Diet 112:1201-10, 2012). As used herein, the term "glycomacropeptide" or "GMP" encompasses both the glycosylated raw form and to the purified GMP polypeptide without the glycosylating moieties.

A number of methods can be used to isolate GMP from whey. Detailed examples of purification methods can be found, for example, in U.S. Pat. No. 5,968,586. Current large-scale technologies to isolate GMP from whey use ion exchange chromatography or ultrafiltration. GMP has an isoelectric point (pI) below 3.8, whereas other major whey proteins have pI values above 4.3. This physicochemical difference between GMP and other whey proteins is commonly used in isolation processes to separate GMP from whey.

Traditional amino acid formula used by individuals who have PKU is free of Phe, which allows an individual with PKU to consume natural foods that contain Phe to meet their daily allowance. However, commercially available GMP contains Phe contaminants from residual whey proteins. The amount of Phe contamination in commercial GMP varies widely (i.e. 5 mg Phe/g product, manufacturer literature, Davisco Foods Intl., Eden Prairie, Minn., U.S.A.; 2.0 mg Phe/g product, Lacprodan cGMP-20 manufacturer literature, Arla Foods, Arhus, Denmark). The method of the present invention can be used by individuals who have PKU, or by the general population of individuals who do not have PKU or any related metabolic conditions. If used by individuals who have PKU, it is preferred that the GMP for use in the present invention contains no more than 2.0 mg Phe/g GMP.

In certain embodiments, commercially obtained GMP may be purified to remove Phe contaminants before being used in the present invention. Possible purification processes are well known in the art, and include without limitation trapping contaminating whey proteins in crude GMP by adsorption onto a cation exchange resin and collecting the purified GMP in the flow-through fraction. Additional techniques known in the art, such as, for example, Ultrafiltration/diafiltration (UF/DF), can be used to concentrate the GMP and wash out peptides, salts, and nonprotein nitrogen. After the purification and concentration steps, a number of techniques known in the art can be used to dry the purified, concentrated GMP, including without limitation lyophilization and spray drying.

This disclosure encompasses a method for increasing the rate of fat oxidation or fat metabolism in a human or non-human animal. The method includes the step of administering an effective amount of a composition comprising glycomacropeptide (GMP) to the animal, wherein the rate of fat oxidation or fat metabolism in the animal is increased.

As used herein, "fat oxidation" and "fat metabolism" are synonymous, and refer to the metabolic pathway in eukaryotic animals by which fats are metabolized to release energy, as manifested by the production of ATP molecules from ADP or by the dissipation of heat. Fat oxidation/metabolism occurs continually, but generally does not become a primary source of energy unless the animal's carbohydrate resources are exhausted, as, for example, during starvation. Fat oxidation/metabolism occurs chiefly in the mitochondria.

"Fats" are lipids, primarily in the form of triglycerides, esters of glycerol and various fatty acids, which serve to store energy within an animal. In fat oxidation/metabolism, the triglycerides are first hydrolyzed to release the fatty acid components. Then, a series of reactions cleave off two carbon atoms at a time from the hydrocarbon chain of the fatty acids. These two-carbon fragments are combined with coenzyme A to form acetyl coenzyme A (acetyl CoA), which then enters the Krebs cycle. The formation of acetyl CoA occurs repeatedly until all the hydrocarbon chain of the fatty acids has been used up.

As used herein, the "rate" of fat oxidation/metabolism refers to the amount of fat oxidized or metabolized in a given unit of time. The rate of fat oxidation/metabolism in an individual can be indirectly measured by, for example, calculating the respiratory exchange ratio (RER) for the individual. The RER is the volume ratio between the respiratory carbon dioxide production and the respiratory oxygen consumption in the individual. Oxygen consumption is calculated by taking the difference between the input oxygen flow and the output oxygen flow (ventilation rates). Similarly, the carbon dioxide production is calculated by taking the difference between the output and input carbon dioxide flows (ventilation rates).

Because carbohydrate molecules have a relatively high oxygen/carbon ratio (about 1:1), while fat molecules have very few oxygen atoms relative to the number of carbon atoms, the metabolism of carbohydrates results in a substantially higher RER than the metabolism of fats (i.e., less outside oxygen is needed to produce the same number of $CO_2$ molecules). Accordingly, if the RER is decreased by a given experimental treatment, that is an indication that the rate of fat metabolism/oxidation has increased relative to the rate of carbohydrate metabolism/oxidation.

This disclosure also encompasses a method for reducing the percentage of body fat in a human or non-human animal. The method includes the step of administering an effective amount of a composition comprising glycomacropeptide (GMP) to the animal, wherein the percentage of body fat in the animal is reduced.

"Percentage of body fat" as used herein refers to the percent of the total weight of an organism that is fat. An increase in the rate of fat metabolism/oxidation would be expected to result in a reduction in the percentage of body fat, as the fat would be converted to energy at a higher rate.

Percentage of body fat can be estimated using several techniques that are well known in the art. For example, in a procedure known as dual energy X-ray absorptiometry, or DXA, X-rays of two different energies are used to scan the body, one of which is absorbed more strongly by fat than the other. Computer software can be used to compare the resulting signals from various points, with the signal differences indicating the amount of fat relative to other tissues at a given point. The sum of signal differences over the entire scan enables the calculation of the overall composition and percentage of body fat of the scanned individual.

There are several other procedures that can be used to accurately determine body fat percentage. Some, referred to as multicompartment models, can include DXA measurement of bone, plus independent measures of body water (using the dilution principle with isotopically labeled water) and body volume (either by water displacement or air plethysmography). As another example, in vivo neutron activation can quantify all the elements of the body and use mathematical relations among the measured elements in the different components of the body (e.g., fat, water, protein) to develop simultaneous equations to estimate total body composition, including body fat. Body fat percentage may also be estimated from average density measurements, bioelectrical impedance analysis, or measurements made of various parameters of the body, such as the circumferences of various body parts or the thicknesses of skinfolds.

This disclosure also encompasses a method for increasing the rate of bone mineralization in a female human or non-human animal. The method includes the step of administering an effective amount of a composition comprising glycomacropeptide (GMP) to the animal, wherein the rate of bone mineralization in the animal is increased.

As used herein, the term "bone mineralization" refer to the process by which mineral, generally in the form of modified calcium hydroxylapatite, is added to the bone's fibrous matrix or scaffolding. The process of bone mineral resorption followed by replacement of bone mineral, with little change in shape of the bone itself, occurs throughout the life of an organism. Thus, continuous bone mineralization is necessary to maintain bone structure and strength over time.

In this context, the term "increasing the rate of bone mineralization" as used herein refers to establishing a greater rate of bone mineralization than would have been established in the absence of GMP in the diet. Accordingly, although the term encompasses an absolute increase in the rate of bone mineralization over time, it also includes scenarios where the rate of bone mineralization decreases less over time than it would have in the absence of GMP in the diet. Similarly, as used herein, the terms "increase in bone mineral content" or "increase in bone mineral density" refer to an organism having a greater bone mineral content or bone mineral density than would have been present in the absence of GMP in the diet. Accordingly, although the terms encompass an absolute increase in the bone mineral content or bone mineral density over time, it also includes scenarios where the bone mineral content or bone mineral density decrease less over time than they would have in the absence of GMP in the diet.

Bone mineral content (BMC) and bone mineral density (BMD) are measured characteristics of bone that are used as indicators of bone mineralization. Both BMD and BMC are used clinically to indirectly measure osteoporosis and fracture risk. BMD is considered a surrogate for bone strength and hence fracture risk. BMD is the amount of mineral matter per square centimeter in a measured cross section of bone, while BMC is the absolute amount of mineral matter in a measured cross section. BMC is derived from the determination of BMD and can be used as a separate indicator of bone mineralization. A variety of methods are known in the art for measuring BMC and/or BMD, including without limitation dual-energy X-ray absorptiometry (DXA or DEXA), quantitative computed tomography (QCT), qualitative ultrasound (QUS), single photon absorptiometry (SPA), dual photon absorptiometry (DPA), digital X-ray radiogrammetry (DXR), and single energy X-ray absorptiometry (SEXA).

This disclosure also encompasses a method for increasing bone strength in a female human or non-human animal. The method includes the step of administering an effective amount of a composition comprising glycomacropeptide (GMP) to the animal, wherein the bone strength in the animal is increased.

As used herein, the term "bone strength" refers generally to the ability of bone to maintain its structural integrity when stressed by an externally applied force. Methods of quantitatively assessing various biomechanical performance parameters related to bone strength are well-known in the art (see, e.g., Turner et al., Bone 14 (1993): 595-608). Such assessment methods can be performed on whole bone, or can be performed at the tissue level.

In this context, the term "increasing bone strength" as used herein refers to the animal having greater bone strength than it would have had in the absence of GMP in the diet. Accordingly, although the term encompasses an absolute increase in bone strength over time, it also includes scenarios where the bone strength of the animal decreases less over time than it would have in the absence of GMP in the diet.

The compositions containing GMP that are used in the method are not limited in form or composition. In certain embodiments, the composition containing GMP is administered orally. Examples of GMP composition forms that can be used in the method include without limitation food products, nutraceuticals, or dietary supplements.

In certain embodiments, the compositions containing GMP are administered in a dosage range covering use as a supplement, as a nutraceutical, or in foods. Preferably, the GMP is administered in a daily dosage range of 0.15-1.0 g GMP per kg of body weight. At the upper end of this range, the dose reflects consumption of GMP as the major source of dietary protein, as occurs in PKU subjects who consume a variety of GMP medical foods. Such foods could also be adapted to the non-PKU population for use in the disclosed method.

As used herein, a "food product" is a composition that can be used or prepared for use as a food, i.e., a composition that can be metabolized by an animal to produce energy and/or build tissue within the animal. Food products made with GMP are known in the art, and are disclosed in, for example, U.S. Patent Application No. 2010/0317597.

As used herein, a "nutraceutical" is a product isolated or purified from foods that is generally sold in a form for oral administration not usually associated with food, and that is demonstrated to have a physiological benefit. In the context of the disclosed method, the physiological benefit is an increase in the rate of fat oxidation/metabolism or a reduction of percentage of body fat. A nutraceutical composition according to the disclosed method may contain only GMP as an active ingredient or, alternatively, may further comprise additional supplemental ingredients, such as vitamins, co-enzymes, minerals, herbs, amino acids, and the like.

Optionally, such compositions include a "nutraceutically-acceptable carrier" which, as referred to herein, is any carrier known in the art to be suitable for oral delivery. Nutraceutical GMP-containing compositions can be in solid or liquid form, including without limitation tablets, powders, capsules, pellets, solutions, suspensions, elixirs, or emulsions. Nutraceutically acceptable carriers also include gums, starches, sugars, cellulosic materials, and mixtures thereof.

The nutraceutical preparations administrable by the disclosed method can be prepared by known dissolving, mixing, granulating, or tablet-forming processes. For oral administration, GMP can be mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

As used herein, a "dietary supplement" is a composition in pill, capsule, tablet, powder or liquid form that is not marketed for use as a conventional food or as the sole item of a meal or diet, but that contains one or more ingredients isolated from conventional food that provides a nutritional benefit (such as GMP).

As used herein, the term "administering" the composition to a human or non-human animal refers to bringing the animal or any of its tissues, organs or cells in contact with the GMP contained in the composition.

As used herein, the term "effective amount" refers to the quantity of active agent (GMP) sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed effective if it resulted in one or more of the following: (a) an increase in the rate of fat oxidation/metabolism; (b) a reduction in percentage of body fat in the animal; (c) an increase in the rate of bone mineralization in the animal; (d) an increase in the bone mineral content or bone mineral density in the animal; or (e) an increase in the bone strength in the animal. Given the guidance provided herein, the optimum effective amounts can be readily determined by one of ordinary skill in the art using routine experimentation.

The composition may be administered to a female human or non-human animal; however, in certain preferred embodiments, the animal is a human. As shown in the Examples below, the inventors have surprisingly determined that the beneficial effects of GMP are significantly greater in female mice than in male mice. Accordingly, in certain embodiments, the animal is female.

As shown in the Examples below, the inventors have surprisingly determined that the method is effective both in individuals having a metabolic disorder such phenylketonuria (PKU) and in individuals unaffected by such disorders. Accordingly, in certain embodiments, the animal to which the composition is administered does not have phenylketonuria (PKU).

The following examples are not intended to limit the scope of the present invention. Various modifications of the disclosed method in addition to those shown and described herein will become apparent to those skilled in the art from the foregoing description and the following examples and fall within the scope of the appended claims.

III. Examples

Example 1

Effect of GMP on Body Fat Percentage and Fat Oxidation/Metabolism in a Murine Model In this example, Applicants demonstrate that (1) female wild type and PKU mice fed a GMP diet showed a significantly lower final fat mass and percent body fat compared with both amino acid and casein diets; (2) both male and female PKU mice fed a GMP diet showed a significantly lower percent of body fat compared with mice fed an amino acid diet, despite similar lean mass and gain in body weight; and (3) both wild type and PKU mice fed a GMP diet had a significantly lower respiratory exchange ratio as compared to mice fed with an amino acid diet, an effect that was most apparent in female mice. The data suggests that the GMP diet increases the rate of fat oxidation/metabolism in the mice.

Introduction.

Our objective was to compare growth, body composition, and energy balance in $Pah^{enu2}$(PKU) and wild type (WT) mice fed low-phe GMP, low-phe AA or high-phe casein diets from 3-23 wks of age. The 2×2×3 design included main effects of genotype, sex and diet. Fat and lean mass were assessed by dual-energy x-ray absorptiometry and acute energy balance was assessed by indirect calorimetry. PKU mice showed growth and lean mass similar to WT littermates fed the GMP or AA diets; however, they exhibited a 3-15% increase in energy expenditure, as reflected in oxygen consumption, and a 3-30% increase in food intake. The GMP diet significantly reduced energy expenditure, food intake and plasma phe concentration in PKU mice compared with the casein diet. Moreover, total fat mass, % body fat and the respiratory exchange ratio ($CO_2$ produced/$O_2$ consumed) were significantly lower in PKU mice fed GMP compared with AA diets.

Materials and Methods.

Animals and Experimental Design.

The animal facilities and protocols reported were approved by the University of Wisconsin-Madison Institutional Animal Care and Use Committee. A PKU mouse colony was established using the murine model of PAH deficiency, the $Pah^{enu}$ mouse, on a C57Bl/6 background (see Harding et al., Gene Ther 13: 457-462, 2006; McDonald et al., Proc Natl Acad Sci USA 87: 1965-1967, 1990). PKU heterozygous mice were bred to produce PKU homozygous mice and WT control mice. Genotyping for the presence of the $Pah^{enu2}$ mutation was performed by PCR analysis of toe biopsy DNA on an amplified region of exon 7 of the PAH gene at 7-10 d of age (TaqMan Gene Expression assay ID AHAAB1X, Applied Biosystems, Inc., Foster City, Calif.). The experimental design included 12 treatment groups in a 2×2×3 factorial design which included 3 main effects and interactions: genotype, PKU homozygous or WT; sex, male or female; and 3 semipurified diets, GMP, AA and casein control. Mice were randomized to the 3 diets by stratified randomization at weaning (21 days), separated by sex, and housed within their litters and dietary treatment groups in shoe-box cages in a room maintained at 22° C. on a 12:12-h light-dark cycle with free access to water. The mice were weighed between 0900-1100 hr five times per week from 21 to 35 d of age and then three times per week through the end of the study.

Mice were fed the experimental diets from weaning through young adulthood for a mean of 20.4±0.11 wk (range 17-23 wk, n=180 mice). Fat mass and lean mass of each mouse was assessed by dual-energy x-ray absorptiometry (DXA) utilizing PIXImus (GE/Lunar Corp, Madison, Wis.). Principally, this quantification is possible by comparing the differential attenuation of two X-ray beams of different intensities through tissue (see Raff et al., Horm Metab Res 33: 151-155, 2001). The scans were analyzed by a single individual blinded to the treatment groups with PIXImus software version 2.10, as previously reported and shown to be strongly correlated with proximate biochemical analysis of soft tissue composition (see Colman et al., J Nutr 137: 2247-2251, 2007; Raff et al., Endocrine 16: 139-143, 2001).

Following anesthesia with isoflurane via an anesthesia machine (IsoFlo, Abbott Laboratories, North Chicago, Ill.), mice were placed prone on the scanner bed with the limbs and tail stretched away from the body. One scan per mouse, requiring 4 min, was performed at 4 different time points, at 6-9, 10-13, 14-17 and 18-21 wk of age. The analysis of each scan excluded the head and provided a serial assessment of lean and fat tissue masses for each mouse throughout the growth cycle.

After consuming the experimental diets for 20 wks, mice were anesthetized using isoflurane via an anesthesia machine and euthanized by exsanguination between 0800-1000 hr in a fed state. Blood was collected by cardiac puncture into syringes containing a final concentration of 2.7 mmol/L EDTA and plasma was isolated by centrifugation at 4° C. The profile of AA in plasma was determined in the Wisconsin State Laboratory of Hygeine using a Hitachi L-8900 AA analyzer equipped with an ion chromatography system using post column ninhydrin derivatization (see Slocum et al., Amino acid analysis of physiological samples. In: Techniques in diagnostic human biochemical genetics: a laboratory manual, edited by F. A. H. New York, N.Y.: Wiley-Liss, 1991, p. 87-126). The samples were deproteinized with sulfosalicylic acid, centrifuged and passed through a 0.2 µm filter before adding an internal standard and injecting into the column.

Diets.

The three experimental diets were formulated to provide equivalent amounts of vitamins, minerals, macronutrients (18% kcal protein, 64-66% carbohydrate and 16-17% fat) and energy (3.8 kcal/g metabolizable energy) and differed only in the source of protein (Harlan Teklad, Madison, Wis.; TD.09667-TD.09669). The composition of the diets is provided in Table 1. The sole source of protein in the diets was provided by 20% (W/W) casein plus 0.3% L-cystine, 17.5% free AA (50), or 20% GMP (BioPURE GMP, Davisco Foods International, Inc., LeSueur, Minn.). The GMP diet was supplemented with 1.5 times the NRC suggested requirement (equivalent to a total supplementation of 2.8% AA) for the following limiting AA to compensate for faster absorption and degradation of AA compared with intact protein (see Ney et al., *J Nutr* 138: 316-322, 2008): arginine, histidine, leucine, methionine, tryptophan and tyrosine. Complete amino acid analysis of the diets was conducted in the Experiment Station Chemical Laboratories, University of Missouri-Columbia (Columbia, Mo.), Table 2. The phe content of the diets expressed per kg diet was casein, 9.2 g phe; AA, 2.2 g phe; and GMP, 2.6 g phe. The low-phe AA and GMP diets provided the minimum level of phe needed to support growth (see Ney et al., *J Nutr* 138: 316-322, 2008).

TABLE 1

Experimental Diets

| Ingredient | Casein | GMP g/kg | Amino Acid |
|---|---|---|---|
| Protein | | | |
| Casein | 200 | | |
| BioPure GMP[1] | | 200 | |
| L-Arginine HCl | | 4.6 | 12.1[2] |
| L-Cystine | 3.0 | | 3.5 |
| L-Histidine, HCl—H$_2$0 | | 3.2 | 4.5 |
| L-Leucine | | 6.8 | 11.1 |
| L-Methionine | | 7.0 | 8.2 |
| L-Phenylalanine | | 0.15 | 2.5 |
| L-Tyrosine | | 5.0 | 5.0 |
| L-Tryptophan | | 1.3 | 1.8 |
| Carbohydrate | | | |
| Sucrose | 250 | 250 | 250 |
| Cornstarch | 241 | 225 | 268 |
| Maltodextrin | 130 | 130 | 130 |
| Cellulose | 50 | 50 | 50 |
| Fat | | | |
| Soybean oil | 70 | 70 | 70 |
| Choline bitartrate | 2.5 | 2.5 | 2.5 |
| Vitamins & Minerals | | | |
| Vitamin mix AIN-93-VX | 13 | 13 | 13 |
| Mineral mix, 98057[3] | 35 | 35 | 35 |
| Sodium chloride | 4.2 | | 3.6 |
| Sodium phosphate, dibasic | 7.2 | | 8.0 |
| Potassium phosphate, dibasic | 2.0 | | 2.0 |
| Calcium phosphate, dibasic | | | 5.25 |
| Calcium phosphate, monobasic | | 9.5 | |
| Calcium carbonate | 13.7 | 6.75 | 9.9 |
| Antioxidant | | | |
| t-Butylhydroquinone | 0.014 | 0.014 | 0.014 |

[1]BioPURE GMP ™; Davisco Foods International, Inc., LeSueur, MN.
[2]In addition, the following L-amino acids were included for a total of 175 g amino acids/kg diet: alanine, 3.5; asparagine, 6.0; aspartic acid, 3.5; glutamic acid, 40; glycine, 23.3; isoleucine, 8.2; lysine HCl, 18.0; proline, 3.5; serine, 3.5; threonine, 8.2; and valine, 8.2, based on Rogers QR and Harper AE, Amino acid diets and maximal growth in the rat. *J Nutr* 87: 267-273, 1965.
[3]Teklad Custom Diets, Madison, WI; mineral mix without calcium and phosphorus.

Metabolic Phenotyping.

Acute energy balance was assessed in a subset of 120 mice at 23 weeks of age with a metabolic phenotyping system utilizing indirect calorimetry (LabMaster modular animal monitoring system, TSE Systems, Chesterfield, Mo.), as previously reported (see Nelson et al., *J Lipid Res* 52: 1723-1732, 2011). Food and water intake, oxygen consumption ($VO_2$) and carbon dioxide production ($VCO_2$) were continuously measured over a 48 hr period and the respiratory exchange ratio (RER, $CO_2/O_2$) was calculated. Mice were acclimated to the individual housing in the metabolic cages prior to data collection as indicated by characteristic circadian rhythms of $O_2$ consumption and $CO_2$ production. Indirect calorimetry measurements ($VO_2$ and $VCO_2$) and the RER from the same time for the 48 h measurement period were averaged and the area under the curve calculated and expressed per 24 hr or during the light (0600-1800 hr) or dark (1801-0559 hr) cycles for each mouse. Oxygen consumption data was expressed per kg of lean mass (see Kaiyala and Schwartz, *Diabetes* 60: 17-23, 2011).

Statistical Analyses.

The primary method of analysis for data obtained at one time point was three-way ANOVA using PROC MIXED, with random effects for animal identification, to identify the main treatment effects of genotype, sex, diet and their interactions followed by the protected least significant differences technique to identify differences among treatment groups (SAS Institute, 2007, Cary, N.C.). Plasma cytokines were analyzed by one-way ANOVA. Changes in body weight were analyzed separately for male and female mice using a repeated measures model within PROC MIXED. The model included the fixed effects of diet, genotype, and sex and all of their interactions, as well as the factor time and all the two-way interactions with the other main effects. A random effect of animal nested within the diet*genotype*sex interaction was also included. In order to account for auto-correlated errors, an autoregressive error structure was included and the Kenward-Roger method was used to compute the denominator degrees of freedom for the tests of the fixed effects. Analysis of longitudinal body composition data and oxygen consumption were each done using a three-way ANOVA that also included age and lean mass, respectively as covariate with interaction terms. Backward elimination was used to remove non-significant terms involving age or lean mass. Statistics were performed on transformed data for results showing unequal variances among groups; actual data are presented when transformations were required. Data are presented as means±SE; $p<0.05$ was considered statistically significant. When significant main effects without significant interaction were observed, data presented in figures were pooled across corresponding treatment groups. Sample size is indicated on the tables and figures.

Results.

Plasma Amino Acid Profile.

Consistent with an absence of PAH activity, the plasma concentration of phe was 15 to 49-fold higher in PKU compared with WT mice, Table 3. The low-phe AA and low-phe GMP diets reduced plasma phe concentration in PKU mice by 65% and in WT mice by 24% compared with the high-phe casein control diets. The plasma concentration of tyrosine was over 50% lower in PKU compared with WT mice and the AA and GMP diets reduced plasma tyrosine concentration by 30-62% in WT and PKU mice compared with the casein diet.

There were alterations in the plasma AA profiles due to diet, consistent with our previous report and the unique AA profiles of the AA, GMP and casein diets (Ney et al., *J Nutr* 138: 316-322, 2008). See Table 2. In both PKU and WT mice, plasma concentrations of glutamine, isoleucine and threonine were significantly higher, and plasma concentration of lysine was significantly lower with ingestion of the GMP compared with the AA and casein diets. Likewise, the plasma concentrations of glycine and serine were significantly higher with ingestion of the AA compared with the GMP and casein diets. Both the casein and GMP diets induced higher plasma concentrations of the large neutral AA, proline, valine and the sum of the branched chain AA, leucine, isoleucine and valine. Female WT and PKU mice showed higher plasma concentrations of arginine, citrulline, lysine and taurine, but lower concentrations of glutamate compared with male mice.

TABLE 2

Amino acid profiles of the three experimental diets

| Amino Acid | Casein | GMP | AA |
|---|---|---|---|
| | | g/kg diet | |
| Alanine | 5.5 | 9.3 | 3.2 |
| Arginine | 6.5 | 4.8 | 8.8 |
| Aspartic acid | 12.5 | 14.2 | 9.0 |
| Cysteine | 3.3 | 0.3 | 3.3 |
| Glutamic acid | 40.0 | 33.0 | 36.5 |
| Glycine | 3.3 | 1.9 | 22.2 |
| Histidine* | 5.5 | 3.1 | 3.1 |
| Isoleucine* | 9.4 | 15.8 | 7.9 |
| Leucine* | 17.2 | 11.4 | 10.5 |
| Lysine* | 14.5 | 10.2 | 14.5 |
| Methionine* | 4.9 | 8.6 | 5.9 |
| Phenylalanine* | 9.2 | 2.6 | 2.2 |
| Proline | 19.0 | 18.5 | 3.8 |
| Serine | 8.9 | 10.2 | 2.4 |
| Threonine* | 7.4 | 24.0 | 7.6 |
| Tryptophan* | 2.7 | 1.6 | 1.9 |
| Tyrosine* | 8.4 | 4.8 | 4.4 |
| Valine* | 11.9 | 13.5 | 7.7 |

*Indispensable amino acids

Growth Rate.

Figure 1B:
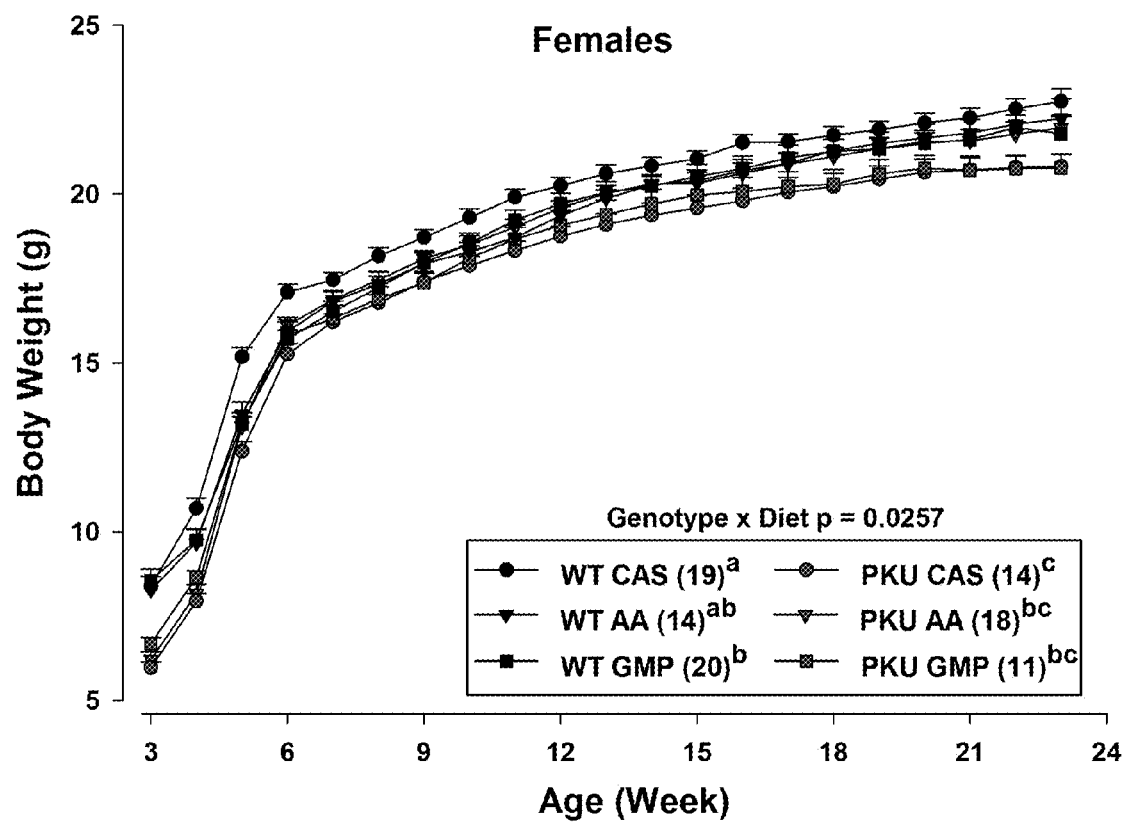
Figure 2A:
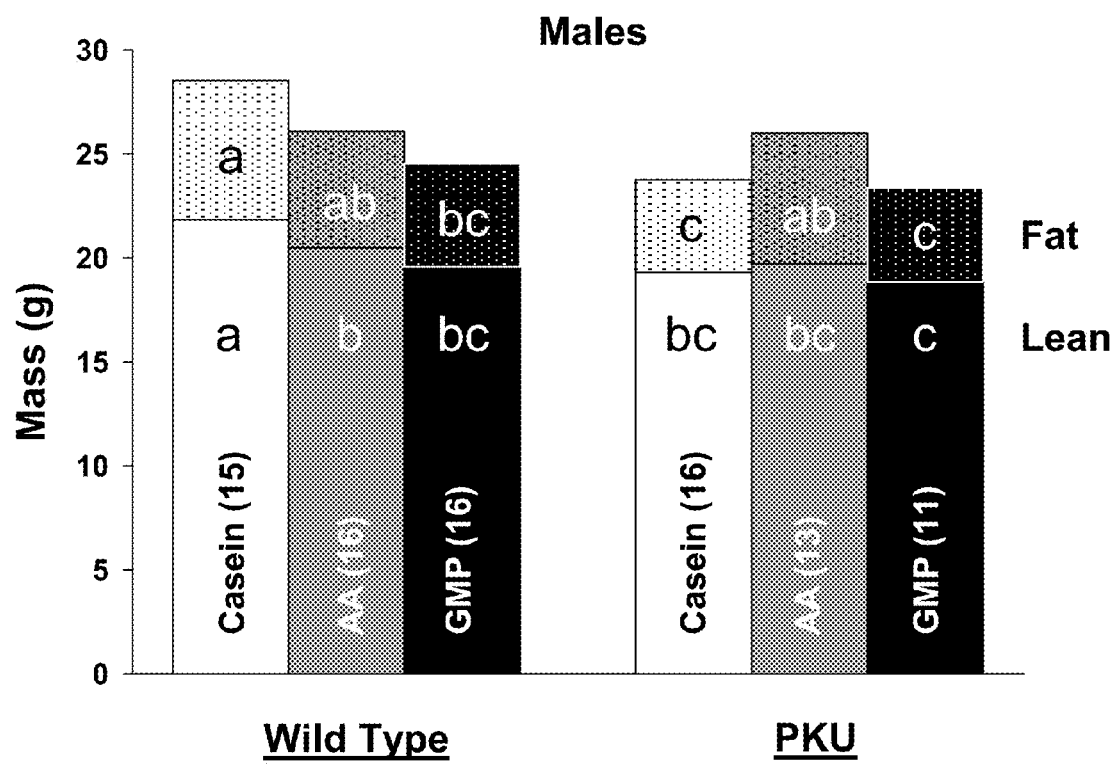
FIGS. 2A-D are graphs showing body composition of lean mass and fat mass determined by dual-energy X-ray absorptiometry in male (FIG. 2A, FIG. 2C) and female (FIG. 2B, FIG. 2D) mice fed casein, AA or GMP diets. Final composition of lean and fat mass was assessed (FIG. 2A, FIG. 2B); means with different superscripts are significantly different (p<0.05). The percentage of body fat was assessed over time (FIG. 2C, FIG. 2D); different letter superscripts indicate significant differences in mean % body fat at the midpoint of time, p<0.05. Male mice showed significant genotype x diet interaction as reflected in presentation of the six groups (FIG. 2A, FIG. 2C). Female mice showed a significant main effect for dietary treatment without significant interaction with genotype as reflected in combining the female WT and PKU dietary groups (FIG. 2B, FIG. 2D). Values in parentheses indicate sample size.
Figure 2B:
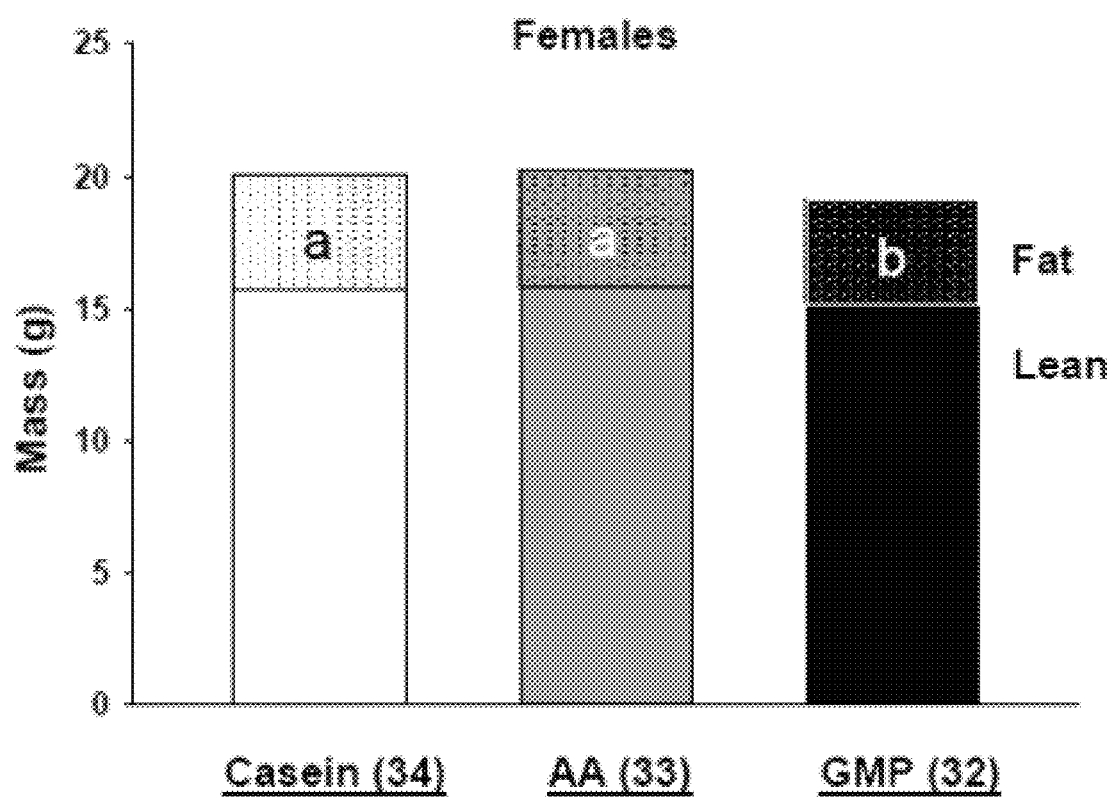
Figure 2C:
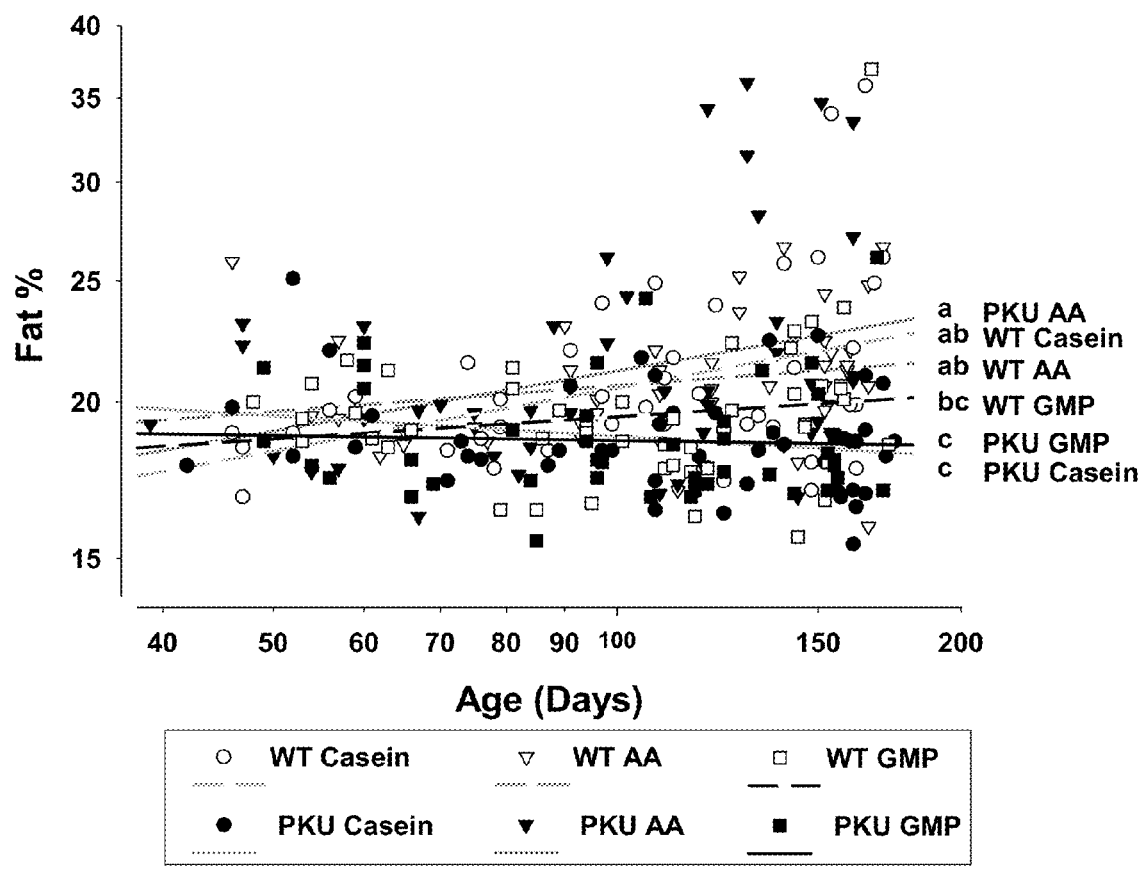
Figure 2D:
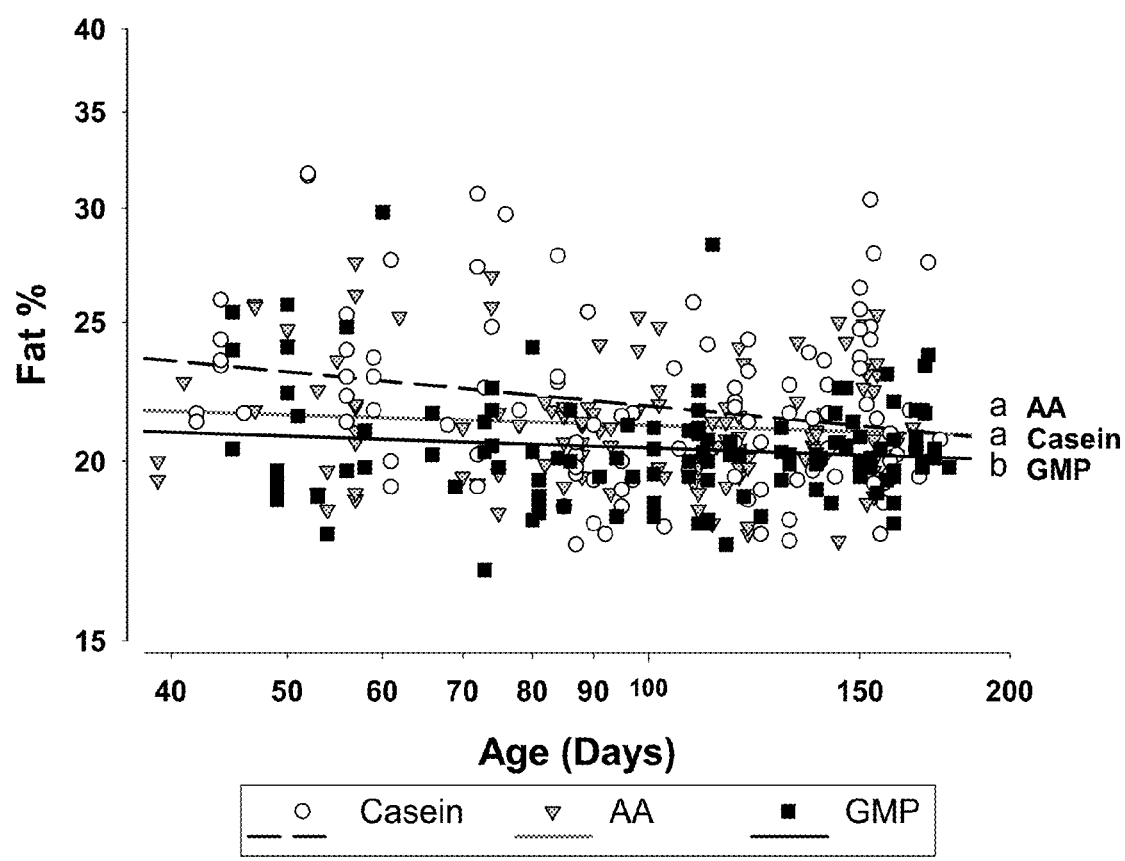

Growth curves showing change in body wt for male and female mice from weaning through 23 wk of age are shown in FIGS. 1A and 1B. At weaning when the experimental diets were initiated, PKU mice weighed 34% less than WT mice (6.2±0.10 vs. 8.4±0.15 grams; p<0.0001). As expected, male mice showed significantly greater accretion of body weight and lean body mass over time than female mice and this response was independent of genotype and diet.

Male WT mice fed the casein diet showed a greater rate of gain in body weight beginning at week five and continuing through the end of the study compared to the other treatment groups. Comparing the entire growth curve of each male treatment group, the only significant difference was that WT males fed the casein diet weighed, on average, 14% more than the other five groups.

In female mice the PKU genotype modulated the growth response such that WT mice weighed significantly more from 14-23 wks than PKU mice. The final body weight of WT female mice was ~3% greater compared with PKU female mice (22.2±0.21 vs 21.6±0.21 g body wt, p=0.0312). Moreover, PKU female mice fed casein weighed the least from wk 4-6, wk 8-13 and during the second half of the growth curve compared with the other 5 treatment groups. With respect to the entire growth curve of each female treatment group, the findings are similar to the male data in that the growth trajectory of WT and PKU mice fed the AA and GMP diets was similar. In addition, WT mice fed casein compared with the low-phe diets showed a greater rate of gain in body wt in association with higher phe intake and plasma phe concentration. Interestingly, female PKU mice did not show a rebound in body weight from weaning while eating the casein diet, as noted in male PKU mice.

Body Composition.

Composition of lean mass and fat mass determined by DXA are shown in FIGS. 2A-D. Coincident with greater body wt, male WT mice fed casein showed a significantly greater amount of lean mass compared with the other five male groups whereas the amount of lean mass in WT and PKU female mice was not significantly different due to diet. Both male and female PKU mice showed a catch up in body weight from weaning and a similar amount of final lean mass compared with their respective WT littermates fed the GMP or AA diets. Thus, the low-phe AA and GMP diets formulations support growth to a similar extent in both WT and PKU mice.

TABLE 3

Concentrations of amino acids in plasma of WT and PKU mice fed diets containing casein, GMP, or amino acids[1]

| | WT mice | | | PKU mice | | | ANOVA p-value[7] | | | |
|---|---|---|---|---|---|---|---|---|---|---|
| | Casein n = 15 | Amino acid n = 13 | GMP n = 13 | Casein n = 14 | Amino acid n = 15 | GMP n = 14 | | | | |
| Amino acid | μmol/L | | | | | | Genotype[2] | Diet[3] | Sex[4] | Gt × Dt[5] |
| Alanine | 754 ± 62 | 1021 ± 97 | 874 ± 110 | 755 ± 67 | 952 ± 112 | 716 ± 63 | | | 0.0364 | |
| Arginine | 95 ± 4 | 93 ± 12 | 83 ± 6 | 73 ± 5 | 87 ± 3 | 79 ± 4 | 0.0087 | | 0.0063 | |
| Aspartate | 14 ± 2 | 11 ± 1 | 13 ± 2 | 10 ± 1 | 7 ± 1 | 8 ± 1 | 0.0033 | | | |
| Citrulline | 76 ± 5 | 68 ± 6 | 75 ± 6 | 78 ± 5 | 70 ± 3 | 64 ± 5 | | | 0.0350 | |
| Cysteine | 17 ± 5 | 6 ± 3 | 5 ± 3 | 9 ± 4 | 5 ± 3 | 2 ± 2 | | 0.0244 | | |
| Glutamate | 29 ± 2 | 32 ± 5 | 41 ± 8 | 28 ± 2 | 27 ± 2 | 40 ± 3 | | 0.0009 | 0.0333 | |
| Glutamine | 474 ± 16 | 533 ± 42 | 661 ± 82 | 434 ± 27 | 475 ± 26 | 541 ± 25 | 0.0337 | <0.0001 | | |
| Glycine | 214 ± 10 | 886 ± 126 | 188 ± 8 | 179 ± 7 | 785 ± 127 | 183 ± 8 | 0.0119 | <0.0001 | | |
| Histidine | 73 ± 3 | 67 ± 4 | 81 ± 14 | 82 ± 4 | 69 ± 5 | 76 ± 2 | | | | |
| Isoleucine | 110 ± 8$^{CD}$ | 83 ± 9$^D$ | 243 ± 30$^A$ | 134 ± 12$^C$ | 95 ± 7$^{CD}$ | 185 ± 24$^B$ | | <0.0001 | | 0.0355 |
| Leucine | 162 ± 12 | 113 ± 11 | 148 ± 16 | 186 ± 20 | 134 ± 10 | 127 ± 5 | | 0.0003 | | |
| Lysine | 437 ± 25 | 447 ± 51 | 372 ± 28 | 415 ± 35 | 470 ± 39 | 339 ± 24 | | 0.0187 | 0.0032 | |
| Methionine | 77 ± 6 | 114 ± 16 | 148 ± 46 | 75 ± 7 | 89 ± 12 | 88 ± 13 | | | | |
| Ornithine | 61 ± 4 | 75 ± 9 | 65 ± 9 | 67 ± 5 | 59 ± 4 | 55 ± 4 | | | | |
| Phenylalanine | 51 ± 2$^C$ | 36 ± 4$^D$ | 41 ± 4$^D$ | 2103 ± 92$^A$ | 722 ± 26$^B$ | 766 ± 18$^B$ | <0.0001 | <0.0001 | | 0.0397 |
| Proline | 157 ± 20 | 90 ± 12 | 242 ± 53 | 203 ± 32 | 81 ± 12 | 167 ± 28 | | <0.0001 | | |
| Serine | 165 ± 10 | 271 ± 24 | 205 ± 35 | 180 ± 11 | 252 ± 13 | 157 ± 12 | | <0.0001 | | |
| Taurine | 500 ± 30 | 589 ± 69 | 561 ± 40 | 417 ± 24 | 488 ± 36 | 489 ± 35 | 0.0097 | | 0.0245 | |
| Threonine | 317 ± 23 | 409 ± 53 | 971 ± 125 | 305 ± 24 | 384 ± 37 | 807 ± 98 | | <0.0001 | | |
| Tryptophan | 61 ± 4 | 75 ± 10 | 72 ± 7 | 64 ± 25 | 52 ± 4 | 65 ± 4 | 0.0033 | 0.0040 | | |
| Tyrosine | 102 ± 11 | 57 ± 12 | 71 ± 17 | 50 ± 7 | 22 ± 3 | 19 ± 3 | <0.0001 | <0.0001 | | |

TABLE 3-continued

Concentrations of amino acids in plasma of WT and PKU mice fed diets containing casein, GMP, or amino acids[1]

| | WT mice | | | PKU mice | | | | | | |
|---|---|---|---|---|---|---|---|---|---|---|
| | Casein n = 15 | Amino acid n = 13 | GMP n = 13 | Casein n = 14 | Amino acid n = 15 | GMP n = 14 | ANOVA p-value[7] | | | |
| Amino acid | μmol/L | | | | | | Genotype[2] | Diet[3] | Sex[4] | Gt × Dt[5] |
| Valine | 315 ± 23 | 219 ± 17 | 401 ± 42 | 352 ± 28 | 227 ± 14 | 333 ± 31 | | <0.0001 | | |
| BCAA[6] | 587 ± 42 | 415 ± 32 | 792 ± 80 | 672 ± 60 | 456 ± 28 | 644 ± 55 | | <0.0001 | | |

[1]Values are means ± SE.
[2]There was a significant genotype effect where wild type mice had higher plasma concentrations of arginine, aspartate, glutamine, glycine, taurine, tryptophan, and tyrosine compared to homozygous mice.
[3]The amino acid diet resulted in higher values for alanine, glycine, and serine compared to casein and GMP. Both amino acid and casein diets had higher values for lysine compared to GMP. The casein diet resulted in higher plasma cysteine than GMP, but not amino acid diet. GMP had higher plasma tryptophan than casein, but not amino acid diet. Casein resulted in higher plasma leucine and tyrosine than both GMP and amino acid diets. Both casein and GMP diets resulted in higher plasma proline, valine, and BCAA than the amino acid diet. The GMP diet resulted in higher plasma glutamate, glutamine, and threonine compared to both the casein and amino acid diets.
[4]Females have higher plasma levels of arginine, citrulline, lysine and taurine, and males have higher plasma glutamate.
[5]There was a significant genotype by diet interaction for isoleucine and phenylalanine. Means in a row with superscripts without a common letter differ, $P < 0.05$.
[6]BCAA, Sum of isoleucine, leucine, and valine.
[7]P-values not listed are non-significant.

Diet had a significant effect on final body fat content and the percent of body weight as fat assessed over time. Male PKU mice showed significantly lower final body fat content as well as percent body fat when fed the GMP or casein diets compared with the AA diet, FIGS. 2A and 2C. In contrast, percent body fat was not significantly different among male WT mice fed the casein, AA or GMP diets. Female WT and PKU mice fed GMP showed a significantly lower final fat mass and percent body fat compared with both the AA and casein diets, FIGS. 2B and 2D. Overall, both male and female PKU mice fed the GMP diet showed a significantly lower percent of body fat compared with mice fed the AA diet, despite similar lean mass and gain in body weight.

PKU Mice Show Increased Energy Expenditure.

Figure 3A:
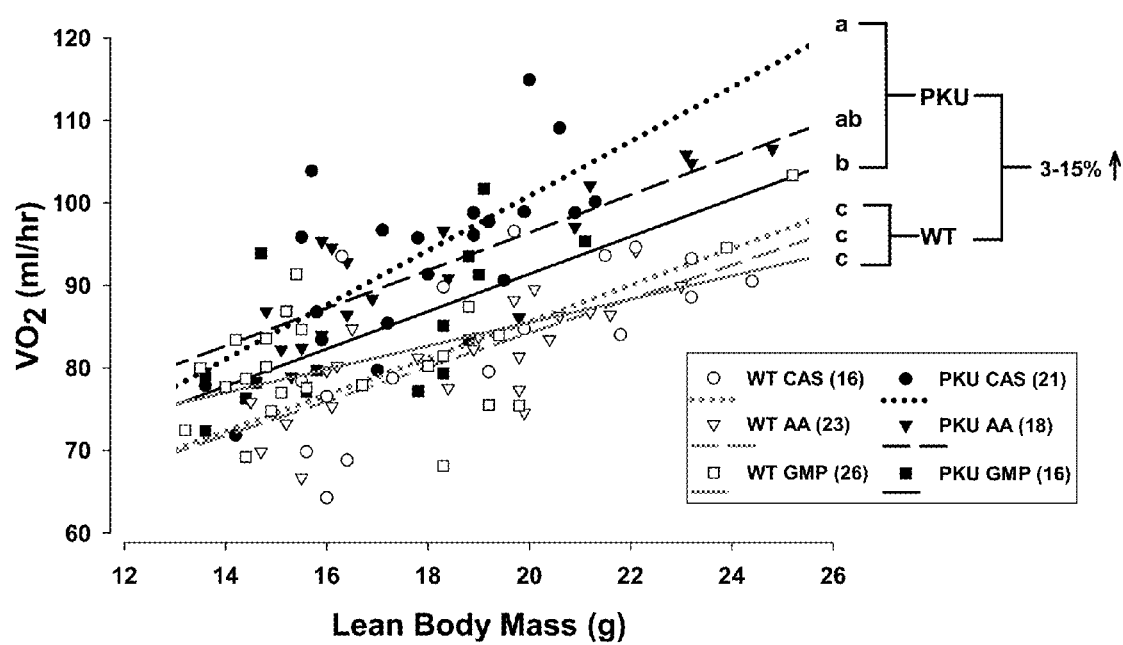
FIGS. 3A and 3B are graphs showing oxygen consumption (FIG. 3A) and food intake (FIG. 3B) in PKU and WT mice fed casein, AA and GMP diets. Oxygen consumption was assessed at 23 wk of age over a 48 hr period and analyzed with lean body mass as a covariate. Mean oxygen consumption showed a significant effect of genotype (P<0.0001) and significant interaction of genotype and diet (p=0.0180) at the mean of lean body mass. Energy expenditure as reflected in oxygen consumption was significantly increased by 3 to 15% in PKU mice compared with WT mice (2.55% increase $GMP^b$; 12.88% increase $AA^{ab}$ and 14.82% increase $casein^a$). Different letter superscripts indicate significant differences in mean oxygen consumption and food intake based on significant genotype x diet interaction. Male mice consumed significantly more food than female mice without diet interaction (p=0.04).
Figure 3B:
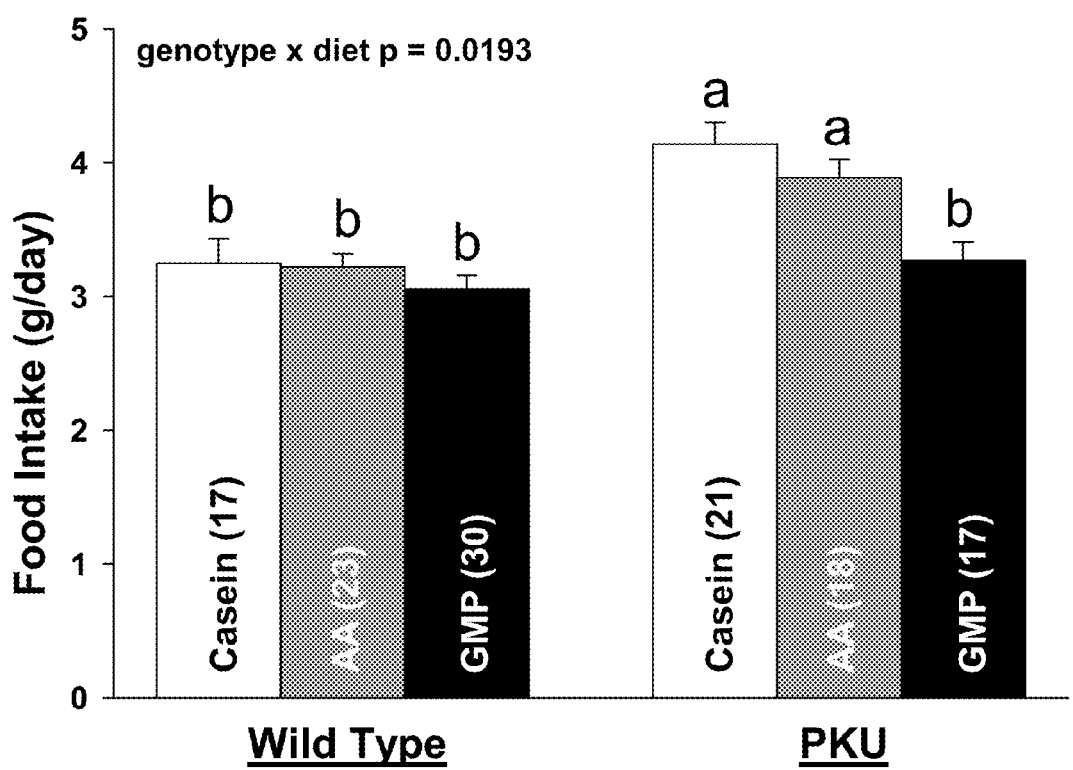
Figure 4A:
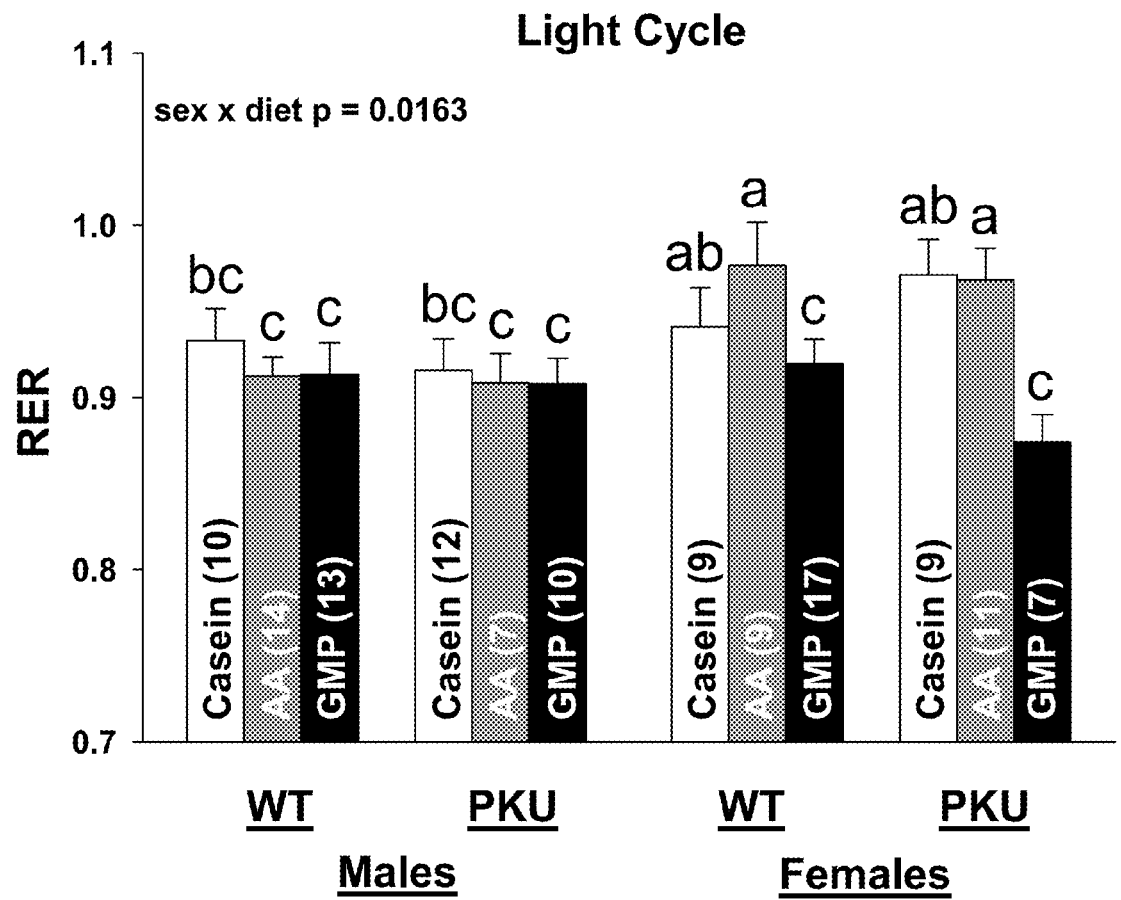
FIGS. 4A and 4B are graphs showing the respiratory exchange ratio (RER, $CO_2$ produced/$O_2$ consumed) during the light (FIG. 4A) and dark cycles (FIG. 4B) in male (WT, C; PKU, E; time course over 24 hr) and female (WT, D; PKU, F; time course over 24 hr) mice fed casein, AA and GMP diets.
Figure 4B:
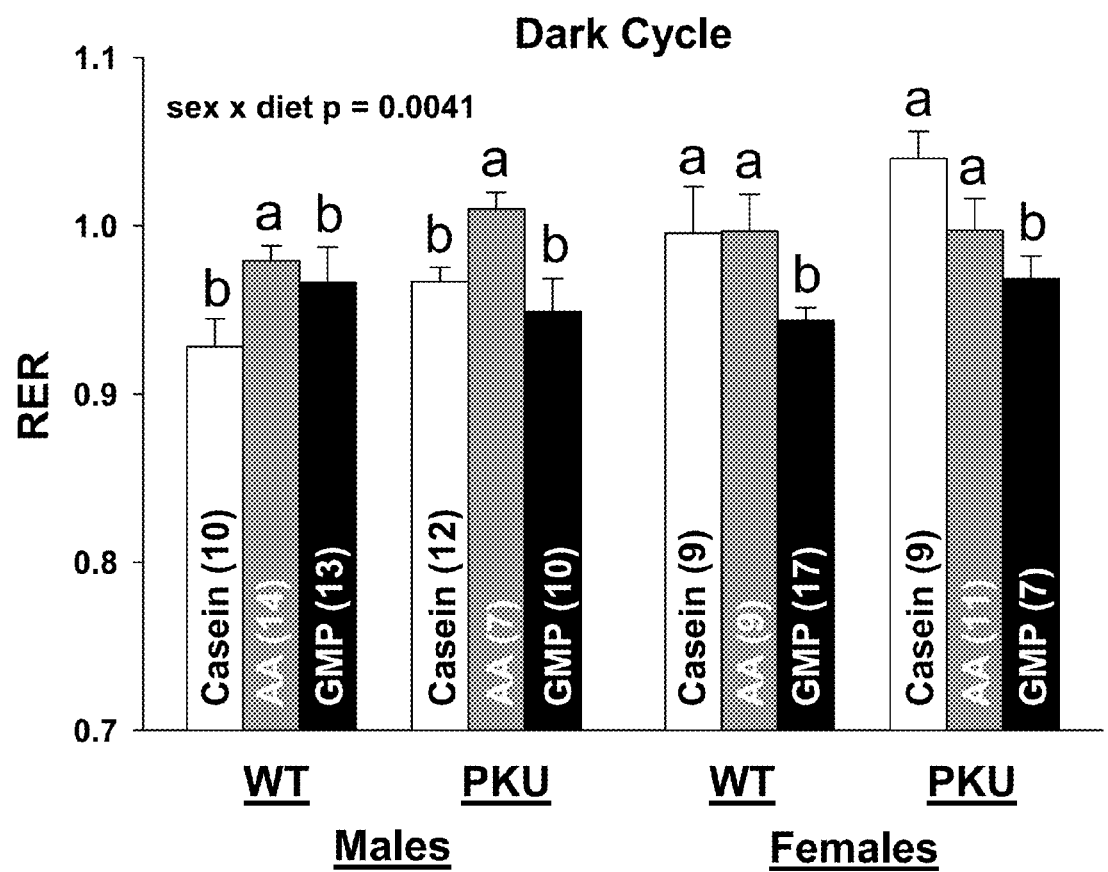
Figure 4C:
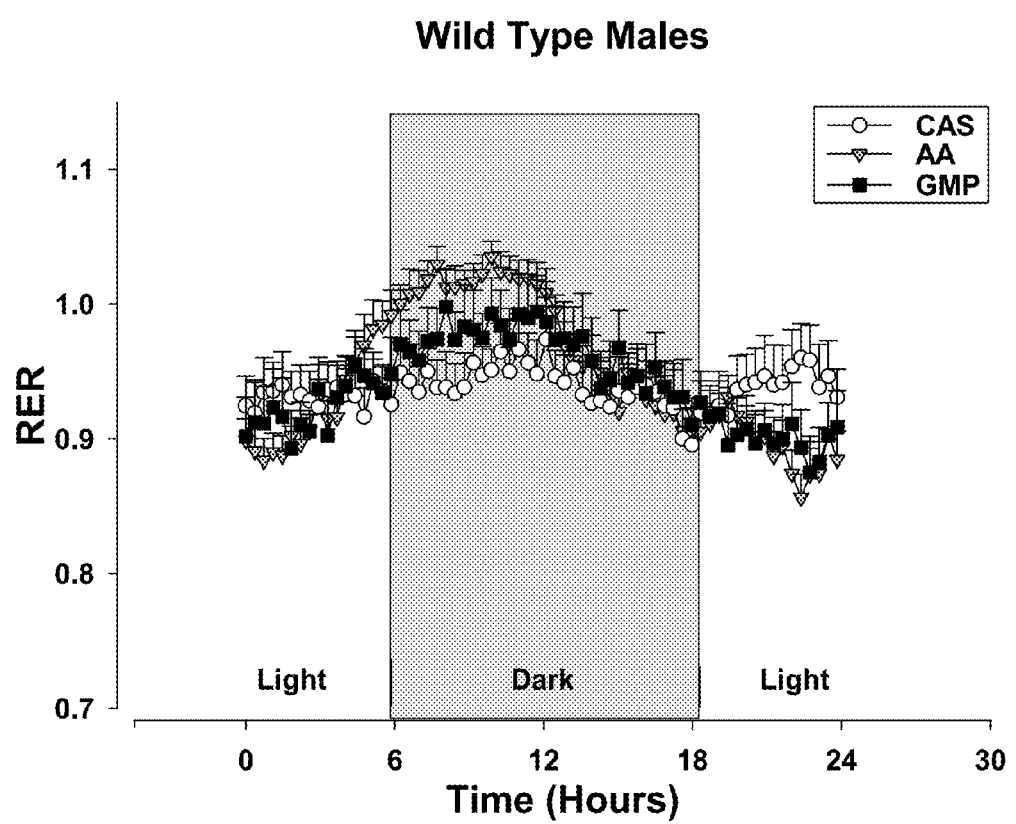
FIG. 4C-E are graphs showing the RER over the 24 hour light-dark-light cycle in wild type male mice (FIG. 4C), wild type female mice (FIG. 4D), PKU male mice (FIG. 4E), and PKU female mice (FIG. 4F). Significant interaction of sex and diet was observed. Values are means±SE; means with different superscripts reflecting the significant interaction of sex and diet are significantly different (p<0.05). During the dark cycle there was a significant effect of genotype with higher RER in PKU vs WT mice (p=0.0380).
Figure 4D:
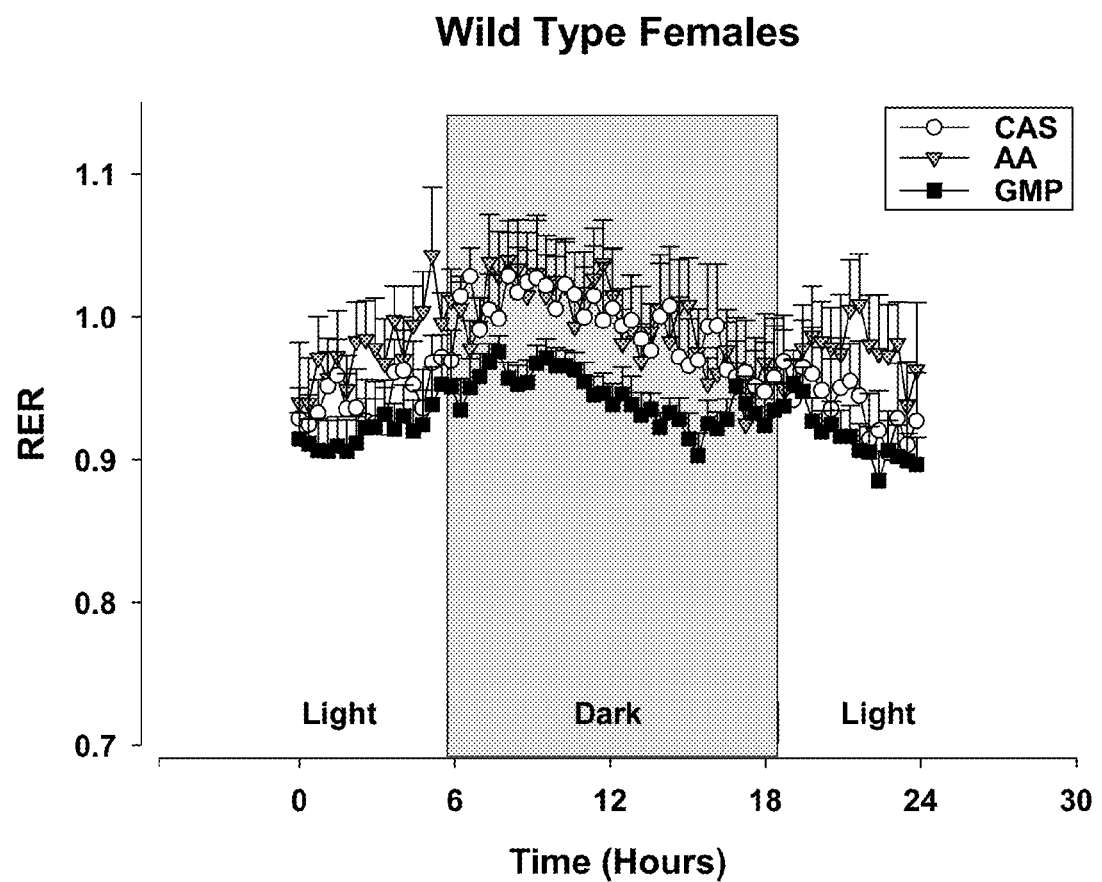
Figure 4E:
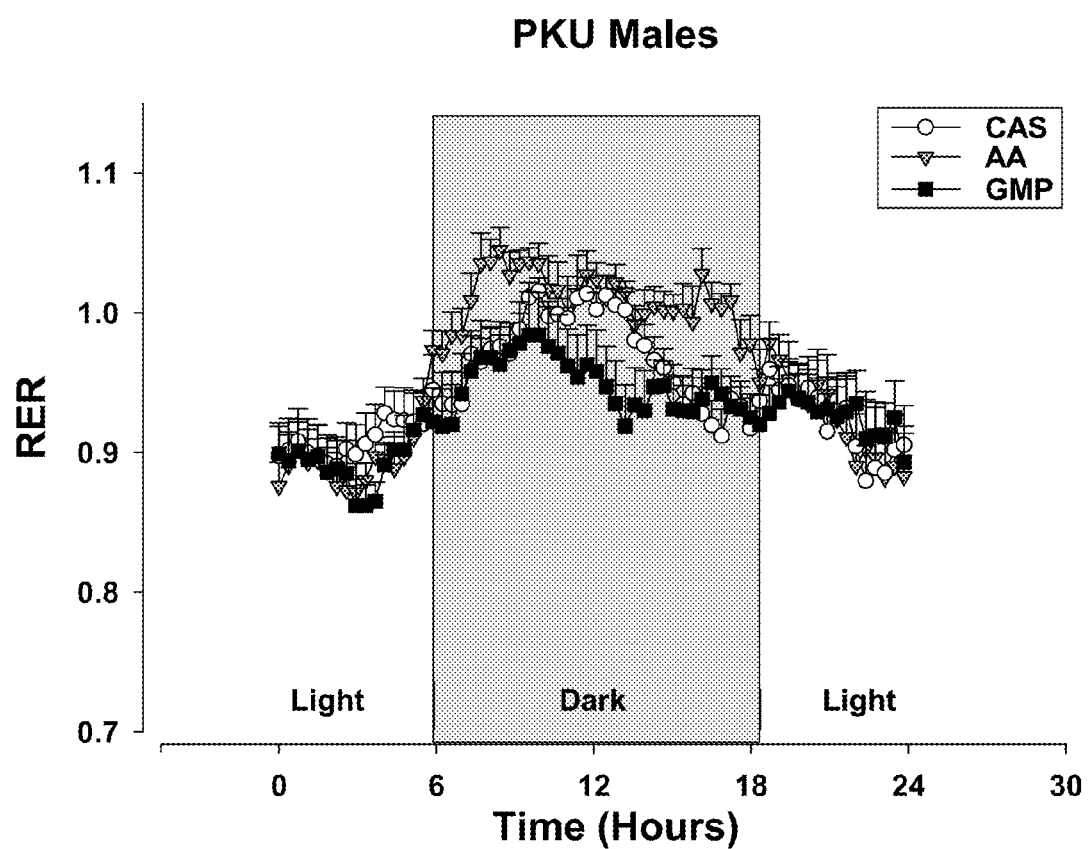
Figure 4F:
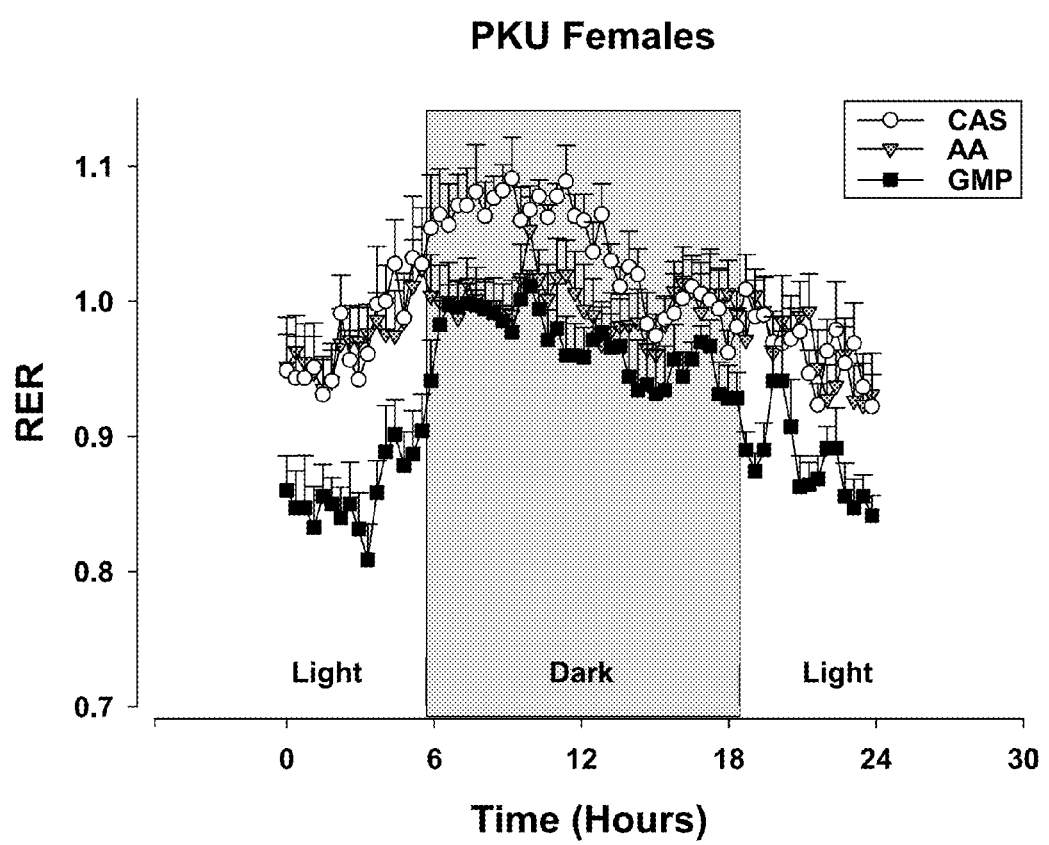

Energy expenditure determined by mean oxygen consumption over 48 hr was significantly increased by 3 to 15% in PKU mice compared with WT mice, FIG. 3A. In PKU mice, the GMP diet significantly attenuated the increase in oxygen consumption induced by the high-phe casein diet (2.55% vs 14.82% increase, p<0.05), although energy expenditure remained significantly higher compared with WT mice. The AA diet did not alter energy expenditure compared with the casein diet in PKU mice (12.88% increase AA diet vs 14.82% increase casein diet compared with WT mice). PKU mice also showed an increase in mean 24 hr energy expenditure compared with WT mice based on oxygen consumption per kg of lean mass (data not shown). Consistent with greater energy expenditure and yet similar growth, food intake was significantly greater in PKU mice fed the casein or AA diets compared to WT mice, FIG. 3B. The GMP diet normalized food intake in PKU mice such that the amount of food eaten by PKU mice to support growth when fed GMP was significantly lower than the amount eaten when fed casein or AA, but not significantly different from that observed in WT mice. Taken together, the oxygen consumption and food intake data demonstrate that the GMP diet supported similar growth and attenuated the metabolic stress that was reflected in increased energy expenditure in PKU mice fed the casein or AA diets.

GMP Diet Reduces the Respiratory Exchange Ratio Compared with the AA Diet.

The RER ($CO_2$ produced/$O_2$ consumed) during the dark cycle when mice were eating was significantly lower in both WT and PKU mice fed the GMP diet compared with the AA diet; significant interaction of sex and diet was observed, FIGS. 4A-4F. The reduction in RER with ingestion of the GMP diet was most apparent in female mice, both WT and PKU, where the RER was significantly reduced during both the light and dark cycles compared to the AA and casein diets. The reduction in RER for male mice, both WT and PKU, fed GMP was only observed during the dark cycle. The lower RER suggests that the GMP diet increased fat oxidation compared with the AA diet. Moreover, it is consistent with the significant reduction in final fat mass observed in female WT and PKU mice fed GMP compared with both the AA and casein diets and in male PKU mice fed GMP compared with the AA diet.

Discussion.

This study assesses the impact of GMP, AA and casein diets fed from weaning through adulthood on growth, body composition, and energy balance in PKU and WT mice. When fed the high-phe casein diet or the low-phe AA diet, PKU mice exhibited metabolic stress, or altered homeostasis induced by the absence of PAH activity, as reflected in increased energy expenditure and food intake compared to WT mice. When PKU mice were fed the low-phe GMP diet, these adverse effects were significantly attenuated.

Evidence in the current example demonstrates that GMP compared with an AA diet significantly lowers RER during the dark cycle in both WT and PKU mice, consistent with increased fat oxidation and supported by a significantly lower percentage of body fat in PKU mice fed GMP. Interestingly, female compared with male mice showed a more pronounced response to the GMP diet in lowering RER and percentage of body fat.

Example 2

Low Bone Strength is a Manifestation of Phenylketonuria and is Attenuated by a Glycomacropeptide Diet Summary.

In this example, we demonstrate that skeletal fragility, as reflected in brittle and weak femora, is an inherent feature of PKU. This PKU bone phenotype is attenuated by a GMP diet as compared with an AA diet. The data suggests that the GMP diet provides some protection against the bone loss associated with PKU.

Phenylketonuria (PKU), caused by phenylalanine (phe) hydroxylase loss of function mutations, requires a low-phe diet plus amino acid (AA) formula to prevent cognitive impairment. Glycomacropeptide (GMP), a low-phe whey protein, provides a palatable alternative to AA formula. Skeletal fragility is a poorly understood chronic complication of PKU. We sought to characterize the impact of the PKU genotype and dietary protein source on bone biomechanics.

Wild type (WT; $Pah^{+/+}$) and PKU ($Pah^{enu2/enu2}$) mice on a C57BL/6J background were fed high-phe casein, low-phe AA, and low-phe GMP diets between 3 to 23 weeks of age. Following euthanasia, femur biomechanics were assessed by 3-point bending and femoral diaphyseal structure was determined. Femoral ex vivo bone mineral density (BMD) was assessed by dual-energy x-ray absorptiometry. Whole bone parameters were used in principal component analysis. Data were analyzed by 3-way ANCOVA with genotype, sex, and diet as the main factors.

Regardless of diet and sex, PKU femora were more brittle, as manifested by lower post-yield displacement, weaker, as manifested by lower energy and yield and maximal loads, and showed reduced BMD compared with WT femora. Four principal components accounted for 87% of the variance and all differed significantly by genotype. Regardless of genotype and sex, the AA diet reduced femoral cross-sectional area and consequent maximal load compared with the GMP diet.

Introduction.

Phenylketonuria (PKU; OMIM 261600) is a recessive genetic disease of amino acid (AA) metabolism caused by loss of function mutations of the gene encoding phenylalanine hydroxylase (EC 1.14.16.1, PAH in humans and Pah in mice), resulting in an inability to convert phenylalanine (phe) to tyrosine [1]. PKU results in gross elevations of phe concentrations in tissue and blood, with downstream cytotoxicity, culminating in profound cognitive impairment if left untreated. Fortunately, this can be averted with lifelong adherence to a low-phe diet that excludes all high protein foods and requires an AA formula to meet nutrient needs [2]. With implementation of newborn screening for PKU in 1960-1970, there are an estimated 50,000 individuals worldwide with treated PKU and a normal range of cognitive function.

Skeletal fragility in early adulthood has emerged as a chronic complication of PKU treated with a low-phe AA diet [3, 4, 5, 6, 7, 8, 9, 10, 11]. Because a low-phe AA diet is the standard of care and is instituted shortly after birth, it remains unknown whether bone fragility in PKU is inherent to the PKU genotype or secondary to its essential dietary management [3].

Compliance with the low-phe diet is often poor after early childhood owing to limited food choices and the bitter taste and strong odor of AA formulas [12, 13, 14, 15]. Moreover, a number of suboptimal outcomes in patients with PKU treated with diet have been identified [16]. Glycomacropeptide (GMP), a whey protein produced during cheesemaking, provides an alternative to AA formula because pure GMP contains no phe and can be made into a variety of low-phe, high protein foods and beverages for those with PKU [17]. Studies in humans with PKU indicate that GMP improves protein retention, phe concentrations, and palabatility of the low-phe diet compared with AA formula [18, 19, 20]. Long term studies in the PKU mouse model ($Pah^{enu2}$) demonstrate that a GMP diet supports similar growth and accretion of lean body mass and attenuates indices of metabolic stress compared with an AA diet [21, 22]. The evidence suggests that the GMP diet provides an acceptable, physiologic source of low-phe dietary protein that may also impact bone development for PKU.

In order to distinguish the contributions of the PKU genotype itself and dietary treatment of the disease, we have conducted a factorial experiment in PKU ($Pah^{enu2/enu2}$) and wild type (WT, $Pah^{+/+}$) mice fed casein, AA and GMP diets. The objective was to characterize the impact of the PKU genotype and dietary protein source on bone biomechanical performance. We assessed the femora by 3 point bending, allowing us to obtain information regarding bone strength (load and stress) and brittleness (displacement and strain), distinct mechanical properties that both contribute to fracture susceptibility [23]. Measuring the bones after testing allowed us to assess the contribution of cross-sectional bone geometry to mechanical performance. This is the first report to rigorously establish the separate contributions of genotype and diet to skeletal fragility in PKU.

Materials and Methods.

Animals and Experimental Design.

The University of Wisconsin-Madison Institutional Animal Care and Use Committee approved the facilities and protocols used in this study. A breeding colony of PKU mice was used to produce experimental animals by breeding C57BL/6J mice heterozygous for the $Pah^{enu2}$ mutation to yield homozygous PKU mice and WT control mice [21, 24]. Experimental mice were genotyped for the presence of the $Pah^{enu2}$ mutation as described previously [22]. The experiment controlled for three main effects and their interactions in a 2×2×3 factorial design: genotype (WT or PKU), sex (male or female), and diet (low-phe GMP and low-phe AA, or high-phe casein) with casein serving as a control diet, FIG. 1A. Mice were randomized to diet, separated by sex and housed within their litters at the time of weaning (21d) in shoe-box cages. Mice had free access to food and water and the facility was maintained at 22° C. on a 12:12-h light-dark cycle.

Mice were fed the experimental diets from weaning through young adulthood (3-25 weeks of age), which resulted in mice being fed diet for 20.4±0.11 weeks on average (range 17-22 weeks of feeding, n=217 mice). The casein, AA and GMP diets were isoenergetic and the source of protein was the only variable manipulated (Harlan Teklad, Madison, Wis.; TD.09667-TD.09669), as previously reported [22]. The casein diet included 20% (wt/wt) casein plus 0.3% L-cystine, the AA diet included 17.5% free AAs [25] and the GMP diet included 20% GMP (BioPURE GMP, Davisco Foods International, LeSueur, Minn.) plus 1.5 times the NRC requirement (equivalent to a total supplementation of 2.8% AA) for 5 limiting AA in order to provide a complete source of protein. The AA profile of the diets was previously reported [22]. All three diets were supplemented with approximately 10% more than NRC requirements for calcium, phosphorus and magnesium to optimize bone growth.

Dual-energy x-ray absorptiometry (DXA) with PIXImus software version 2.10 (GE/Lunar Corp, Madison, Wis.) was performed to obtain in vivo whole body bone mineral density (BMD) and bone mineral content (BMC) at the end of the experiment. Mice were anesthetized with isoflurane with an anesthesia machine (IsoFlo, Abbott Laboratories, North Chicago, Ill.) and placed prone on the DXA scanner bed with their tail and appendages fully extended. Each mouse received one scan at the completion of the study. Handling of the data obtained from the DXA scan was performed by a single scientist blinded to the treatment groups and subsequent statistical analysis of the densitometry data was performed by the authors. Once mice completed the feeding study, they were placed under anesthesia using an isoflurane anesthesia machine and euthanized by exsanguination via cardiac puncture. Following euthanasia, both femora were dissected free of soft tissue, wrapped in phosphate buffered saline-saturated gauze, and stored at −80° C. Specimens were subjected to two freeze thaw cycles, one prior to DXA, and the second prior to biomechanical testing. Prior to biomechanical analysis, femora were gradually warmed by placing them at 4° C. for at least 12 hours, and then allowing them to come to room temperature prior to analysis. Bones were broken in two different sessions. Prior to bone fracture femur length of the second block of femora (n=78 mice) was measured using Vernier calipers measuring the distance between the greater trochanter and the medial condyle.

Biomechanical Testing.

We measured areal BMD of isolated femora by DXA as previously described [26]. Femoral BMD was measured twice with repositioning and we tested femoral diaphysis biomechanical performance by quasi-static 3-point bending under displacement control at a rate of 0.3 mm/sec, with a support span of 7.5 mm as previously described, FIG. 1B. This produces a mid-diaphyseal fracture directly below the crosshead. By using the femoral condyles and the $3^{rd}$ trochanter as anatomical landmarks to position bones consistently, the testing protocol produces highly reproducible fractures. We obtained the periosteal perimeter, cortical cross-sectional area, outer and inner major and minor axis lengths, shape factor (ratio of outer major axis length to outer minor axis length), and cross-sectional moment of inertia in the fracture plane from digital photographs [27]. We used the geometric properties and the whole bone mechanical testing data to calculate the material properties of the bone tissue according to the standard beam theory equations [23], using the averages of both femora for further analysis: Stress ($\sigma$), (MPa)=FLc/4/I with F=force, L=length, c=outer radius in the plane of bending, and I=cross-sectional moment of inertia in the plane of bending. Strain ($\epsilon$), (mm/mm)=12cd/$L^2$ with c=outer radius in the plane of bending, d=displacement, L=length. Young's Modulus (E), (MPa)=(F/d)($L^3$/48I), with F=force, L=length, and I=cross sectional moment of inertia in the plane of bending.

Principal Component Analysis.

The following input variables were included in principal component analysis (PCA): Body mass, femoral BMD, post-yield deflection, total deflection, yield load, maximum load, energy, stiffness, femoral cross-sectional area, femoral periosteal perimeter, femoral inner major and minor axis lengths, femoral outer major and minor axis lengths, femoral diaphyseal shape factor, and femoral diaphyseal cross-sectional moment of inertia. The PCA was performed with the SAS function proc princomp (SAS Institute, Cary, N.C.) [28, 29, 30]. We performed further analysis of the principal components (PCs) with Eigen values ≥1. PC values for each animal were calculated by multiplying each PC's Eigenvector by the animal's parameter vector.

Statistical Analysis.

Data were analyzed by three-way ANOVA or ANCOVA using PROC MIXED. Femur biomechanics occurred at two different times, thus a random effect of time as a blocking factor was included in the model. The three-way ANCOVA tested for main effects of genotype, sex, and diet as well as their two and three way interactions. Femoral cross section measurements and biomechanics data were adjusted for the animal's body mass by including body mass as a covariate. When body mass wasn't a significant predictor for a parameter the term was removed and results from a subsequent three-way ANOVA are presented. Differences between treatment groups were detected using a protected Fisher's Least Significant Difference (LSD) test (SAS Institute, 2007, Cary, N.C.). Data transformations were performed where appropriate to fit assumptions of normality and equal variance prior to statistical analysis. If data transformations failed, a respective non-parametric ANCOVA or ANOVA was performed on ranked data. Untransformed data are presented in the tables. Data are analyzed per animal; biomechanical data are an average of the right and left femora. Data are presented as mean±SE. P-values <0.05 are considered significant. Where there was no significant interaction, data were pooled into treatment groups by their respective significant main effects.

Results.

Growth and Whole Body Bone Mineral Density.

The low-phe AA and GMP diets significantly reduced plasma phe concentration in both WT and PKU mice, Table 4. In spite of restricting dietary phe to the minimum needed to support nearly normal growth, plasma phe concentration in PKU mice remained abnormally elevated, approximately 14-fold higher in PKU compared with WT mice. Regardless of diet, whole body BMD was significantly lower in PKU compared with WT mice. Regardless of sex, femur length was significantly shorter in WT mice fed the AA diet compared with the GMP and casein diets, and not significantly different from PKU mice. Plasma phe concentration did not predict femur length, whole body BMD or BMC.

TABLE 4

In vivo measurements.

| | Wild Type Mice | | | | | |
|---|---|---|---|---|---|---|
| | Males | | | Females | | |
| Variable | Casein | AA | GMP | Casein | AA | GMP |
| N | 17 (10) | 18 (7) | 19 (7) | 23 (9) | 16 (4) | 22 (10) |
| Body Mass (g)$^{a,b,c,e,g}$ | 31.1 ± 0.8 | 28.5 ± 0.5 | 28.1 ± 0.8 | 22.5 ± 0.3 | 22.5 ± 0.3 | 21.9 ± 0.4 |
| ᵗPlasma phe (µmol/L)$^{a,c,e}$ | 51.5 ± 4.5 | 38.5 ± 7.0 | 41.0 ± 0.0 | 50.2 ± 1.6 | 34.3 ± 6.1 | 41.9 ± 2.2 |
| BMC (mg)$^{a,c,d,f}$ | 574 ± 13 | 533 ± 12 | 528 ± 13 | 533 ± 18 | 527 ± 16 | 602 ± 14 |
| BMD (mg/cm$^2$)$^{a,b,f}$ | 51.4 ± 0.3 | 50.7 ± 0.4 | 50.2 ± 0.6 | 51.6 ± 0.6 | 51.4 ± 0.6 | 52.2 ± 0.4 |
| Length (mm)$^{a,b,e}$ | 16.91 ± 0.01 | 16.86 ± 0.02 | 16.91 ± 0.01 | 16.89 ± 0.02 | 16.84 ± 0.02 | 16.88 ± 0.01 |

TABLE 4-continued

In vivo measurements.

| | PKU Mice | | | | | |
|---|---|---|---|---|---|---|
| | Males | | | Females | | |
| Variable | Casein | AA | GMP | Casein | AA | GMP |
| N | 18 (7) | 16 (5) | 14 (6) | 19 (6) | 20 (4) | 13 (3) |
| Body Mass (g)$^{a,b,c,e,g}$ | 26.2 ± 0.4 | 29.5 ± 1.0 | 26.8 ± 0.7 | 21.4 ± 0.4 | 22.0 ± 0.3 | 21.5 ± 0.5 |
| $^r$Plasma phe (µmol/L)$^{a,c,e}$ | 2026 ± 151 | 726 ± 61 | 745 ± 26 | 2206 ± 76 | 719 ± 19 | 786 ± 24 |
| BMC (mg)$^{a,c,d,f}$ | 571 ± 16 | 504 ± 14 | 555 ± 15 | 489 ± 16 | 495 ± 11 | 542 ± 8 |
| BMD (mg/cm$^2$)$^{a,b,f}$ | 49.8 ± 0.3 | 50.1 ± 0.7 | 48.2 ± 0.6 | 48.5 ± 0.5 | 50.4 ± 0.3 | 49.9 ± 0.6 |
| Length (mm)$^{a,b,e}$ | 16.86 ± 0.01 | 16.84 ± 0.03 | 16.85 ± 0.01 | 16.83 ± 0.01 | 16.87 ± 0.02 | 16.81 ± 0.01 |

Values are means ± SE;
N, no of mice for measurement of body mass;
BMC, whole-body bone mineral content;
BMD, whole-body bone mineral density.
$^r$Data analyzed by 3 way ANOVA on ranked data.
$^a$genotype effect,
$^b$sex effect,
$^c$diet effect,
$^d$gt*sex effect,
$^e$gt*diet effect,
$^f$sex*diet effect,
$^g$gt*sex*diet effect.
Body mass: WT female mice weighed more than PKU female mice. WT males fed casein and PKU males fed AA weighed the most. There was no difference in body mass between WT males fed AA and WT or PKU males fed GMP, and PKU males fed casein weighed the least.
Plasma phe: PKU mice had higher plasma phe than WT mice. Among PKU mice, there as a significant reduction in plasma phe with the GMP or AA diet. Among WT mice, there was also a significant reduction in plasma phe with the GMP or AA diet.
BMC: Females fed GMP and males fed casein had the highest BMC. There was no difference between females fed casein and males or females fed AA, but males fed GMP had a higher BMC than females fed AA. There was a significant reduction in BMC in PKU females compared to either WT females or WT and PKU males.
BMD: PKU animals had a lower BMD compared to WT animals. Males fed GMP had a lower BMD compared to females fed GMP or AA and males fed casein. Females fed casein had a lower BMD than females fed GMP.
Length: Males had longer femurs than female mice. WT mice fed AA had a significant reduction in femur length compared to WT mice fed GMP and casein. Moreover, PKU mice fed casein, AA and GMP had significantly shorter femurs than WT mice fed GMP and casein, but were not different from WT mice fed AA.
Numbers in parenthesis indicate sample size from femur length analysis.

Femora of PKU Mice Have Decreased Strength and Increased Brittleness.

Figure 5A:
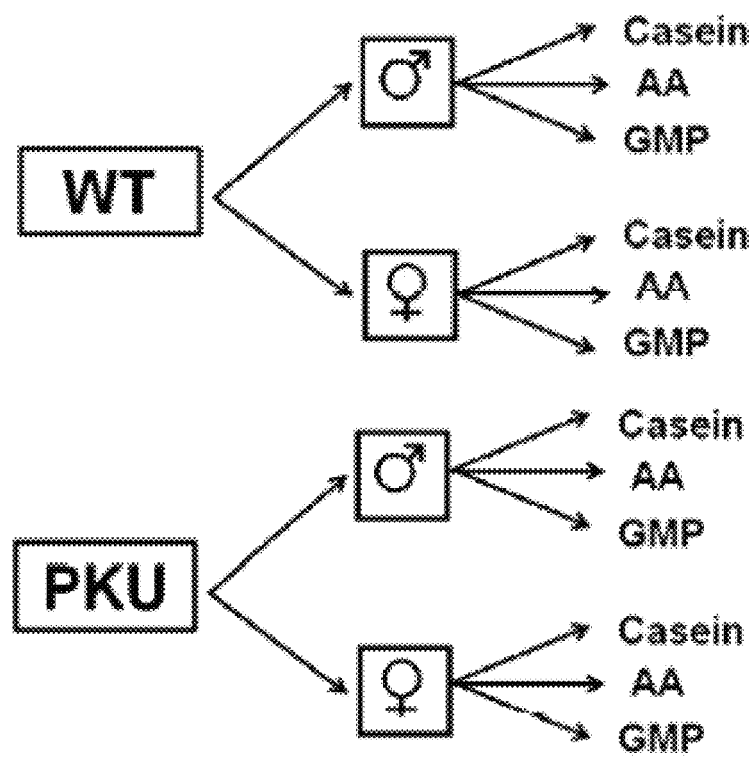
FIGS. 5A and 5B illustrate the experimental design and three-point bending test described in the example. The experiment utilized a 2×2×3 factorial design with a total of 12 groups (see FIG. 5A schematic). A cartoon of the three-point bending test of a mouse femur and a representative photograph are shown in FIG. 5B.
Figure 5B:
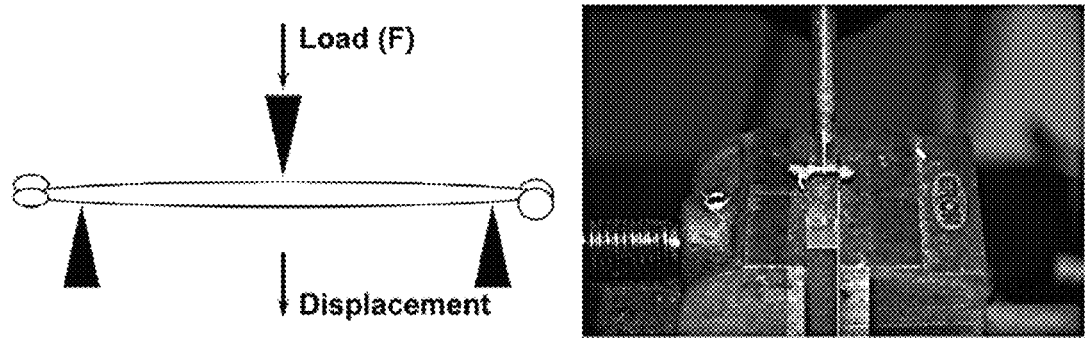
Figure 6:
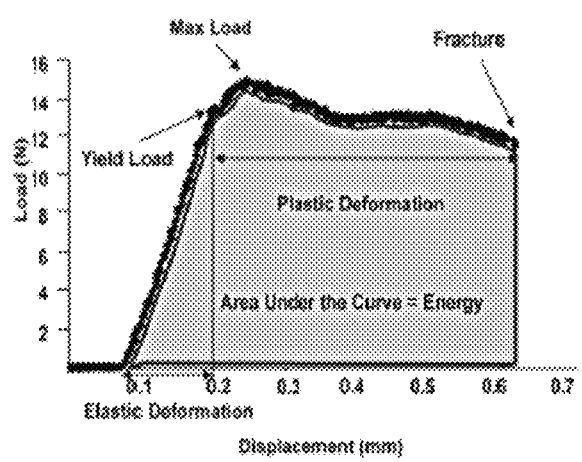
FIGS. 6A-H are graphs of data from the load-displacement curve analysis of WT and PKU mice. Schematic of a load-displacement curve generated from the three-point bending test from which the yield point, maximum load, elastic and plastic deformation, and energy to failure (shaded area under the curve) are obtained (FIG. 6A). Representative load-displacement curves for WT and PKU mice (FIG. 6B). Effects in WT and PKU mice for yield load (FIG. 6C), maximum load (FIG. 6D), post-yield displacement (PYD) (FIG. 6E), total displacement (FIG. 6F), energy to failure (FIG. 6G), and femoral bone mineral density (BMD) (FIG. 6H). Values are means±SE; p-values represent main effect of genotype. Sample size is shown in parenthesis. All values for femoral biomechanical performance had a significant main effect for genotype, WT>PKU.
Figure 6:
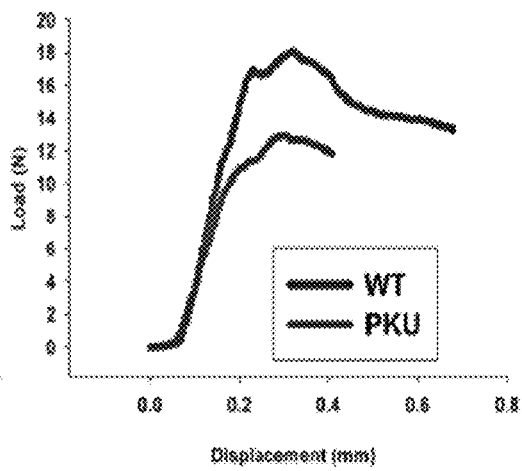
Figure 6:
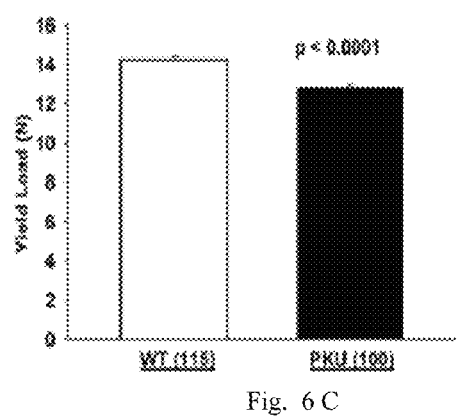
Figure 6:
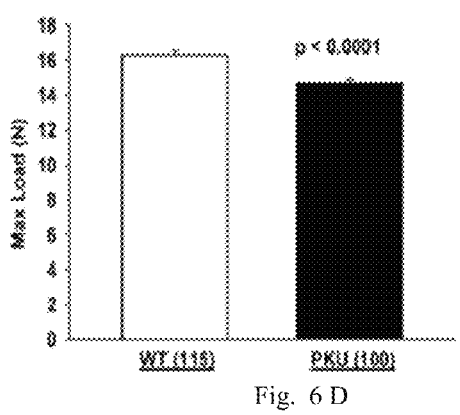
Figure 6:
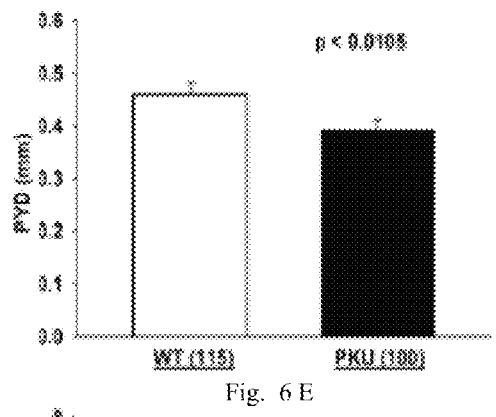
Figure 6:
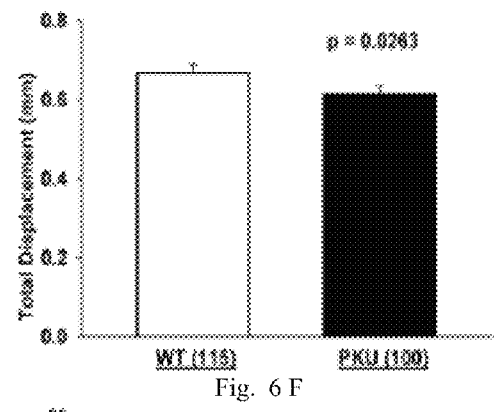
Figure 6:
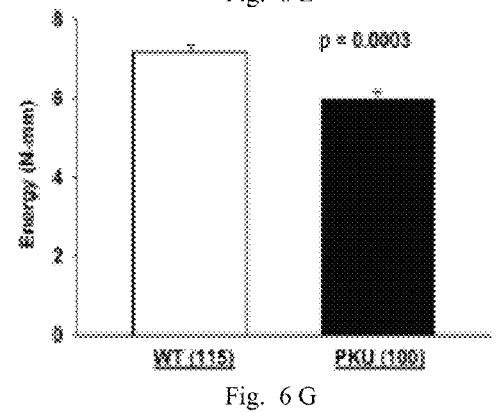
Figure 6:
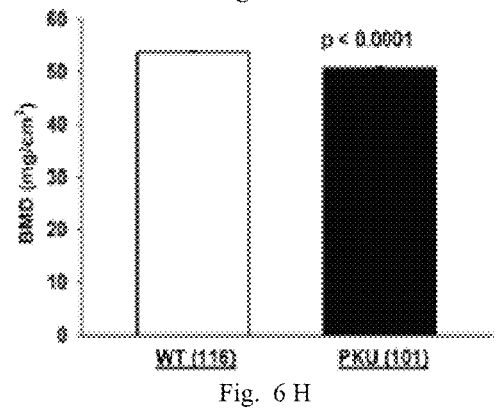

The 3-point bending test produces mid-diaphyseal fractures under controlled loading conditions (FIG. 5B). The primary analysis of the test measures 3 elements of biomechanical performance: displacement (the amount the bone bends), strength (load, or the force applied to the bone), and absorbed energy (the area under the load-displacement curve), as summarized in FIG. 5A and Table 5. Representative load-displacement curves for a WT and PKU femur are shown in FIG. 6B. Following fracture, specimen geometry in the plane of the fracture is assessed (Table 6), allowing calculation of the corresponding tissue-level mechanical properties (Table 7) from standard beam equations, as described in the methods section. The raw data reflect the biomechanical performance of the actual bone, while the tissue level or material properties (i.e., tissue properties and material properties are synonyms) reflect the performance of an idealized sample of the bone tissue, independent of its size and shape.

TABLE 5

Force-displacement curve analysis showing whole bone biomechanical performance.

| | Wild Type Mice | | | | | |
|---|---|---|---|---|---|---|
| | Males | | | Females | | |
| Variable | Casein | AA | GMP | Casein | AA | GMP |
| N | 17 | 18 | 19 | 23 | 16 | 22 |
| $^r$PY disp (mm)$^{a,b}$ | 0.48 ± 0.04 | 0.51 ± 0.07 | 0.55 ± 0.08 | 0.38 ± 0.04 | 0.45 ± 0.04 | 0.40 ± 0.03 |
| $^r$Total disp (mm)$^{a,b}$ | 0.69 ± 0.04 | 0.74 ± 0.07 | 0.78 ± 0.07 | 0.57 ± 0.04 | 0.65 ± 0.04 | 0.61 ± 0.04 |
| *$^r$Stiffness (N/mm)$^{a,b,d,g}$ | 87 ± 4 | 80 ± 2 | 78 ± 4 | 110 ± 5 | 94 ± 5 | 102 ± 3 |
| *$^r$Yield load (N)$^{a,b}$ | 13.7 ± 0.6 | 13.5 ± 0.3 | 12.9 ± 0.4 | 15.2 ± 0.5 | 14.8 ± 0.4 | 15.2 ± 0.4 |
| *$^r$Max load (N)$^{a,b,c,d}$ | 15.8 ± 0.5 | 15.0 ± 0.3 | 14.6 ± 0.4 | 18.1 ± 0.5 | 16.6 ± 0.4 | 17.6 ± 0.4 |

TABLE 5-continued

Force-displacement curve analysis showing whole bone biomechanical performance.

| *'Energy (N-mm)[a] | 7.54 ± 0.37 | 7.01 ± 0.55 | 7.15 ± 0.61 | 6.87 ± 0.44 | 7.09 ± 0.39 | 7.33 ± 0.46 |

| | PKU Mice | | | | | |
| --- | --- | --- | --- | --- | --- | --- |
| | Males | | | Females | | |
| Variable | Casein | AA | GMP | Casein | AA | GMP |
| N | 18 | 16 | 14 | 19 | 20 | 13 |
| 'PY disp (mm)[a,b] | 0.47 ± 0.05 | 0.43 ± 0.06 | 0.46 ± 0.07 | 0.38 ± 0.05 | 0.31 ± 0.03 | 0.30 ± 0.04 |
| 'Total disp (mm)[a,b] | 0.69 ± 0.05 | 0.65 ± 0.06 | 0.70 ± 0.06 | 0.61 ± 0.05 | 0.51 ± 0.03 | 0.55 ± 0.04 |
| *'Stiffness (N/mm)[a,b,d,g] | 78 ± 4 | 74 ± 4 | 79 ± 7 | 75 ± 2 | 89 ± 3 | 81 ± 3 |
| *'Yield load (N)[a,b] | 11.7 ± 0.4 | 12.3 ± 0.4 | 12.6 ± 0.4 | 13.0 ± 0.5 | 13.2 ± 0.4 | 14.3 ± 0.5 |
| *'Max load (N)[a,b,c,d] | 14.1 ± 0.4 | 14.1 ± 0.4 | 14.6 ± 0.6 | 14.8 ± 0.4 | 15.3 ± 0.3 | 16.2 ± 0.4 |
| *'Energy (N-mm)[a] | 6.61 ± 0.50 | 5.86 ± 0.50 | 6.56 ± 0.65 | 5.90 ± 0.53 | 5.31 ± 0.30 | 5.71 ± 0.37 |

Values are means ± SE;
N, no of mice;
PY, post-yield; disp, displacement;
N, newtons.
*Data analyzed using ANCOVA with a covariate of body mass.
'Data transformed to satisfy assumptions of normality and variance.
'Non-transformable data was ranked.
[a] genotype effect,
[b] sex effect,
[c] diet effect,
[d] gt*sex effect,
[e] gt*diet effect,
[f] sex*diet effect,
[g] gt*sex*diet effect.

PY disp: Males had a greater PY disp than females. WT mice had a greater PY disp than PKU mice. Total disp: Males had a greater total disp than females. WT mice had a greater total disp than PKU mice.
Stiffness: All female groups except PKU females fed GMP or casein had stiffer bones than males. Among female groups WT females fed casein and GMP had the stiffest bones. There was no difference between female mice fed AA diet and female PKU mice fed GMP, however PKU females fed casein had a significant reduction in stiffness. Among male mice the only significant difference was a reduction in stiffness in male PKU mice fed AA compared to WT males fed casein.
Yield load: Female mice tolerated a higher load at the yield point than male mice. WT mice tolerated a higher load at the yield point compared to PKU mice.
Max Load: Females had a greater maximum load before fracture compared to males. Moreover, WT females had a greater max load than PKU females, however there were no difference between genotypes for the males. Mice fed the GMP diet had a significant increase in maximum load compared to mice fed the AA diet, but there was no difference between mice fed the GMP and casein diets, additionally there was no difference between mice fed the casein and AA diets.
Energy: It required more energy to fracture the femurs of WT mice than it did to fracture the femurs of PKU mice.

TABLE 6

Size, shape, and content of mice femora.

| | Wild Type Mice | | | | | |
| --- | --- | --- | --- | --- | --- | --- |
| | Males | | | Females | | |
| Variable | Casein | AA | GMP | Casein | AA | GMP |
| N | 17 | 18 | 19 | 23 | 16 | 22 |
| *'CSA (mm$^2$)[b,c,d] | 1.07 ± 0.04 | 0.97 ± 0.03 | 0.97 ± 0.02 | 1.01 ± 0.02 | 0.98 ± 0.04 | 0.96 ± 0.02 |
| *'Perimeter (mm)[b,c] | 6.07 ± 0.12 | 5.78 ± 0.12 | 5.80 ± 0.10 | 5.60 ± 0.05 | 5.47 ± 0.08 | 5.37 ± 0.04 |
| *'Inner Minor Axis (mm)[a,b,c,e] | 0.93 ± 0.03 | 0.90 ± 0.02 | 0.91 ± 0.02 | 0.89 ± 0.01 | 0.85 ± 0.01 | 0.84 ± 0.01 |
| *'Inner Major Axis (mm)[c,e] | 1.68 ± 0.05 | 1.60 ± 0.05 | 1.64 ± 0.04 | 1.48 ± 0.02 | 1.46 ± 0.02 | 1.41 ± 0.02 |
| *'Outer Minor Axis (mm)[b,c,e] | 1.34 ± 0.03 | 1.27 ± 0.02 | 1.29 ± 0.02 | 1.32 ± 0.01 | 1.27 ± 0.02 | 1.27 ± 0.01 |
| *'Outer Major Axis (mm)[c] | 2.25 ± 0.05 | 2.11 ± 0.05 | 2.11 ± 0.09 | 2.02 ± 0.02 | 1.97 ± 0.03 | 1.93 ± 0.02 |
| *Shape Factor (unitless)[b] | 1.68 ± 0.02 | 1.66 ± 0.03 | 1.64 ± 0.02 | 1.54 ± 0.02 | 1.55 ± 0.02 | 1.52 ± 0.01 |

TABLE 6-continued

Size, shape, and content of mice femora.

| | | | | | | |
|---|---|---|---|---|---|---|
| *$^r$CSMI (mm$^4$)$^{bce}$ | 0.19 ± 0.01 | 0.16 ± 0.01 | 0.17 ± 0.01 | 0.17 ± 0.01 | 0.16 ± 0.01 | 0.15 ± 0.00 |
| $^t$BMD (mg/cm$^2$)$^{a,b,d}$ | 54.0 ± 0.7 | 51.9 ± 0.6 | 51.8 ± 0.7 | 55.0 ± 0.8 | 54.1 ± 0.9 | 55.0 ± 0.5 |
| BMC (mg)$^{a,b}$ | 29.2 ± 0.6 | 27.3 ± 0.5 | 27.0 ± 0.6 | 27.8 ± 0.6 | 27.1 ± 0.5 | 27.5 ± 0.4 |

| | PKU Mice | | | | | |
|---|---|---|---|---|---|---|
| | Males | | | Females | | |
| Variable | Casein | AA | GMP | Casein | AA | GMP |
| N | 18 | 16 | 14 | 19 | 20 | 13 |
| *$^t$CSA (mm$^2$)$^{b,c,d}$ | 0.96 ± 0.02 | 0.95 ± 0.09 | 1.00 ± 0.04 | 0.90 ± 0.02 | 0.91 ± 0.02 | 0.94 ± 0.02 |
| *$^r$Perimeter (mm)$^{b,c}$ | 5.80 ± 0.07 | 5.60 ± 0.09 | 5.72 ± 0.12 | 5.49 ± 0.07 | 3.34 ± 0.06 | 5.38 ± 0.07 |
| *$^r$Inner Minor Axis (mm)$^{a,b,c,e}$ | 0.92 ± 0.01 | 0.88 ± 0.02 | 0.87 ± 0.01 | 0.93 ± 0.01 | 0.86 ± 0.01 | 0.88 ± 0.02 |
| *$^t$Inner Major Axis (mm)$^{c,e}$ | 1.62 ± 0.03 | 1.54 ± 0.03 | 1.49 ± 0.04 | 1.49 ± 0.03 | 1.41 ± 0.02 | 1.41 ± 0.03 |
| *$^r$Outer Minor Axis (mm)$^{b,c,e}$ | 1.29 ± 0.01 | 1.25 ± 0.02 | 1.27 ± 0.02 | 1.31 ± 0.01 | 1.24 ± 0.01 | 1.28 ± 0.02 |
| *$^t$Outer Major Axis (mm)$^c$ | 2.11 ± 0.03 | 2.06 ± 0.04 | 2.10 ± 0.05 | 1.93 ± 0.03 | 1.90 ± 0.03 | 1.92 ± 0.02 |
| *Shape Factor (unitless)$^b$ | 1.64 ± 0.02 | 1.65 ± 0.03 | 1.65 ± 0.02 | 1.49 ± 0.01 | 1.53 ± 0.02 | 1.50 ± 0.02 |
| *$^t$CSMI (mm$^4$)$^{bce}$ | 0.16 ± 0.01 | 0.15 ± 0.01 | 0.16 ± 0.01 | 0.16 ± 0.01 | 0.14 ± 0.00 | 0.15 ± 0.01 |
| $^t$BMD (mg/cm$^2$)$^{a,b,d}$ | 50.8 ± 0.6 | 50.5 ± 0.9 | 51.1 ± 0.8 | 49.8 ± 0.7 | 51.2 ± 0.4 | 51.3 ± 0.7 |
| BMC (mg)$^{a,b}$ | 26.0 ± 0.5 | 25.5 ± 0.8 | 25.6 ± 0.7 | 23.3 ± 0.6 | 24.6 ± 0.3 | 24.4 ± 0.7 |

Values are raw data means ± SE;

N, no of mice;

CSA, cross sectional area;

CSMI, cross sectional moment of inertia;

BMD, areal bone mineral density;

BMC, bone mineral content.

*Data analyzed using ANCOVA with a covariate of body mass.

$^t$Data transformed to satisfy assumptions of normality and variance.

$^r$Non-transformable data was ranked.

$^a$genotype effect, $^b$sex effect, $^c$diet effect, $^d$gt*sex effect, $^e$gt*diet effect, $^f$sex*diet effect, $^g$gt*sex*diet effect.

CSA: WT females had a greater CSA than PKU females, both of which were greater than the males per unit body weight. A main effect of diet demonstrated a significant reduction in CSA in mice fed the AA diet.

Perimeter: Females had a larger perimeter than males. Mice fed casein had the greatest perimeter, followed by GMP, and then AA.

Inner minor axis (IMA): Females had a larger IMA than males. PKU mice fed casein had the largest IMA. There was no difference between WT mice fed casein and WT or PKU mice fed GMP. Mice fed GMP were also not different from mice fed AA, however PKU mice fed AA had a significantly smaller IMA compared to WT mice fed casein.

Inner Major Axis (IMAJA): Mice fed the casein diet had the greatest IMAJA.

Outer minor axis (OMA): Females had a greater OMA than males. PKU mice fed casein had the longest OMA and PKU mice fed AA had the shortest.

Outer major axis (OMAJA): Mice fed casein had a larger OMAJA than mice fed either GMP or AA diet.

Shape factor (SF) = OMAJA/OMA: Females had a more circular cross section than males.

CSMI: Females had a larger CSMI compared to males after correction for body weight. PKU mice fed casein had the greatest CSMI. There was no difference in CSMI between WT mice fed casein, WT and PKU mice fed GMP and WT mice fed AA, however there was a significant reduction in CSMI in PKU mice fed AA. There also was no difference between WT and PKU mice fed casein or GMP.

BMD: WT females had a higher BMD than WT males, both of which were higher than the BMD of PKU mice, where there were no differences due to gender or diet.

BMC: Male mice had a greater BMC than females. WT mice had a greater BMC than PKU mice.

TABLE 7

Stress-strain curve analysis showing tissue level biomechanical performance.

| | Wild Type Mice | | | | | |
|---|---|---|---|---|---|---|
| | Males | | | Females | | |
| Variable | Casein | AA | GMP | Casein | AA | GMP |
| N | 17 | 18 | 19 | 23 | 16 | 22 |
| *[r]Yield strain (unitless)[c,e] | 0.030 ± 0.002 | 0.031 ± 0.002 | 0.031 ± 0.002 | 0.028 ± 0.001 | 0.028 ± 0.001 | 0.028 ± 0.001 |
| [r]PY strain (unitless)[a,b] | 0.068 ± 0.005 | 0.070 ± 0.011 | 0.076 ± 0.012 | 0.053 ± 0.005 | 0.061 ± 0.005 | 0.054 ± 0.005 |
| *[r]Total strain (unitless)[e] | 0.098 ± 0.006 | 0.101 ± 0.011 | 0.107 ± 0.011 | 0.080 ± 0.006 | 0.089 ± 0.006 | 0.083 ± 0.005 |
| *Modulus (MPa)[a,c,d,e,g] | 4184 ± 256 | 4543 ± 234 | 4305 ± 231 | 5670 ± 202 | 5374 ± 223 | 6017 ± 184 |
| *[r]Yield stress (MPa)[a,b,c] | 92 ± 3 | 102 ± 4 | 96 ± 3 | 111 ± 3 | 115 ± 4 | 121 ± 3 |
| *[r]Max stress (MPa)[a,b,c,e,f] | 105 ± 3 | 113 ± 4 | 109 ± 3 | 131 ± 3 | 129 ± 4 | 141 ± 3 |
| [r]Toughness (MPa)[a] | 7.14 ± 0.29 | 6.97 ± 0.40 | 7.19 ± 0.51 | 6.95 ± 0.43 | 7.51 ± 0.47 | 7.87 ± 0.45 |
| *[r]Failure stress (MPa)[e] | 80 ± 4 | 76 ± 7 | 72 ± 6 | 99 ± 5 | 91 ± 5 | 105 ± 3 |

| | PKU Mice | | | | | |
|---|---|---|---|---|---|---|
| | Males | | | Females | | |
| Variable | Casein | AA | GMP | Casein | AA | GMP |
| N | 18 | 16 | 14 | 19 | 20 | 13 |
| *[r]Yield strain (unitless)[c,e] | 0.031 ± 0.002 | 0.029 ± 0.002 | 0.032 ± 0.002 | 0.031 ± 0.001 | 0.026 ± 0.001 | 0.034 ± 0.003 |
| [r]PY strain (unitless)[a,b] | 0.064 ± 0.007 | 0.058 ± 0.008 | 0.061 ± 0.009 | 0.054 ± 0.008 | 0.041 ± 0.004 | 0.041 ± 0.006 |
| *[r]Total strain (unitless)[e] | 0.095 ± 0.007 | 0.087 ± 0.008 | 0.093 ± 0.008 | 0.085 ± 0.008 | 0.067 ± 0.003 | 0.075 ± 0.005 |
| *Modulus (MPa)[a,c,d,e,g] | 4236 ± 253 | 4386 ± 173 | 4520 ± 274 | 4314 ± 145 | 5768 ± 234 | 4915 ± 281 |
| *[r]Yield stress (MPa)[a,b,c] | 86 ± 2 | 98 ± 2 | 98 ± 3 | 103 ± 3 | 112 ± 4 | 117 ± 4 |
| *[r]Max stress (MPa)[a,b,c,e,f] | 104 ± 2 | 112 ± 2 | 113 ± 3 | 118 ± 3 | 130 ± 3 | 133 ± 4 |
| [r]Toughness (MPa)[a] | 6.74 ± 0.50 | 6.13 ± 0.45 | 6.84 ± 0.63 | 6.39 ± 0.49 | 5.95 ± 0.31 | 6.39 ± 0.45 |
| *[r]Failure stress (MPa)[e] | 76 ± 5 | 84 ± 5 | 82 ± 4 | 92 ± 5 | 104 ± 4 | 106 ± 5 |

Values are means ± SE;
N, no of mice;
PY, post-yield;
MPa, megapascals.
*Data analyzed using ANCOVA with a covariate of body mass.
[t]Data transformed to satisfy assumptions of normality and variance.
[r]Non-transformable data was ranked.
[a]genotype effect,
[b]sex effect,
[c]diet effect,
[d]gt*sex effect,
[e]gt*diet effect,
[f]sex*diet effect,
[g]gt*sex*diet effect.

Yield strain: PKU mice fed GMP and casein had the highest strain at their yield point and PKU mice fed AA had the lowest. There was no difference between WT mice fed the three diets and PKU mice fed AA. Additionally, there was no difference between WT mice fed GMP and AA with PKU mice fed casein.
PY strain: Males had a greater strain after yielding than females. WT mice had a greater strain after yielding than PKU mice.
Total strain: PKU mice fed AA had a significant reduction in total strain and there was no difference across all other groups.
Modulus: The three way interaction demonstrated that females tended to have bones with a higher intrinsic stiffness than males; WT females fed GMP and PKU females fed AA had a higher modulus than WT and PKU males fed GMP as well as PKU males fed casein. Additionally, WT females fed casein or AA had a higher modulus than PKU males fed GMP. Among females, PKU mice fed casein had a significant reduction in intrinsic stiffness, moreover WT females fed all three diets and PKU females fed AA had a higher modulus than PKU females fed GMP. Among males, PKU mice fed casein had a significant reduction in modulus compared to male mice fed AA and there was no difference across the other five groups.
Yield stress: Wild type mice tolerated more stress before yielding compared to PKU mice. Female mice tolerated more stress before yielding compared to male mice. Mice fed AA and GMP tolerated more stress before yielding compared to mice fed casein.

TABLE 7-continued

Stress-strain curve analysis showing tissue level biomechanical performance.

Max stress: Female groups fed GMP and AA had a higher max stress before fracture compared to male groups and female mice fed casein had a higher max stress than males fed casein. Among females, groups fed GMP had the highest max stress, followed by AA and then casein. Among males, groups fed AA had a higher max stress than males fed casein, but males fed GMP were not different from the other two. PKU mice fed casein had a significant reduction in max stress compared to WT and PKU mice fed GMP and AA as well as WT mice fed casein.
Toughness: WT mice had tougher bones than PKU mice, as measured by area under the stress strain curve.
Failure stress: PKU mice fed AA had a higher stress at fracture compared to WT mice fed AA and PKU mice fed casein. WT mice fed casein and PKU mice fed GMP also had a higher stress at fracture compared to PKU mice fed casein.

Regardless of sex or diet, the PKU genotype was associated with reduced femoral biomechanical properties assessed by three-point bending (FIGS. 6B-H). Yield load, or the force required to elicit permanent damage to the femur, and the maximum load achieved before fracture were significantly lower in PKU mice. Total displacement, or the total amount of deformation by the femur before fracture, was also reduced in PKU compared with WT mice. The post-yield displacement, a measurement of ductility, was significantly lower with PKU, thus the femora of PKU mice are more brittle (i.e., the opposite of ductile) and yield sooner than WT femora. Additionally, the energy required to fracture the bone, measured as the area under the load-displacement curve, was significantly reduced in PKU femora. These measures of whole bone biomechanical performance are paralleled by the tissue level analysis of the stress-strain relationship (Table 7). This suggests an inherent disturbance in the strength of PKU bone independent of size. Moreover, decreases in mineralization are supported by ex vivo DXA data. Both areal BMD as well as BMC of femora (Table 6) are significantly reduced in PKU mice compared with WT mice. In summary, the femora in PKU mice are more brittle, weaker, and absorb less energy than those of WT mice.

We sought evidence regarding whether plasma phe levels are related to bone status. We found no significant relationship between plasma phe and any biomechanical or BMD outcomes (data not shown).

Dietary Protein Source Modifies the PKU Bone Phenotype.

Figure 7:
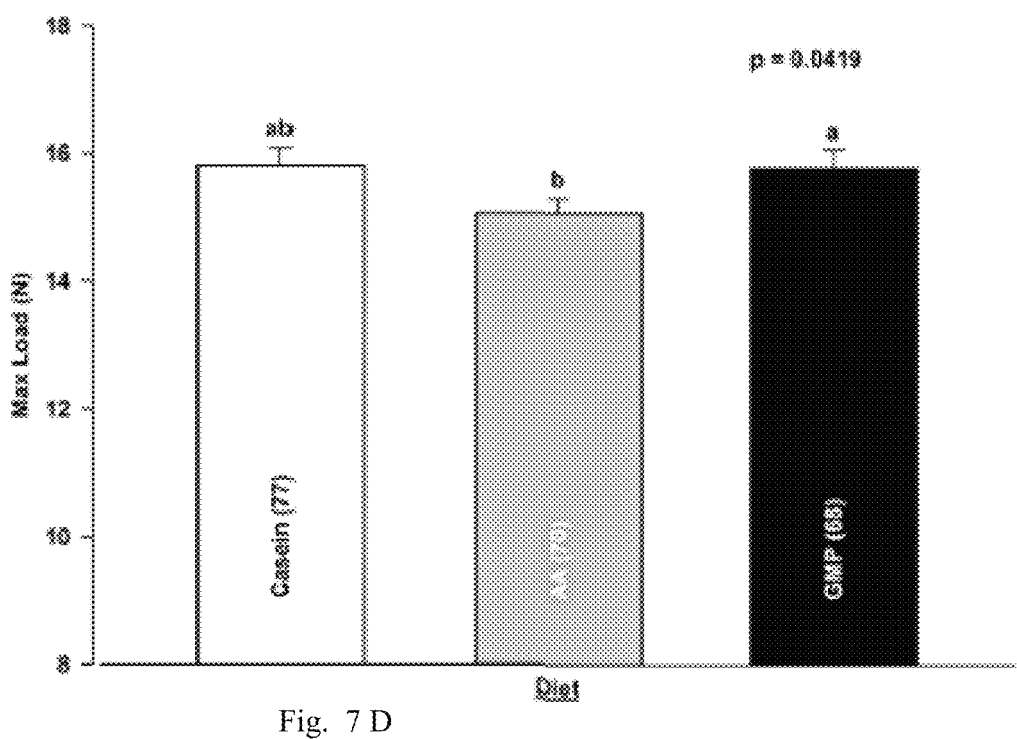
FIGS. 7A-D illustrates that diet modifies femoral size and strength in WT and PKU mice. Representative photographs of femoral cross-sectional geometry in mice fed casein, AA, and GMP diets (FIG. 7A) from which measurements of cross-sectional area (FIG. 7B) and perimeter (FIG. 7C) are obtained. A graph showing diet effect on maximum load derived from load-displacement curve analysis is shown in FIG. 7D. Values are means±SE; p-values represent main effect of diet. Sample size is shown in parenthesis. Groups with different letter superscripts are significantly different (p<0.05).

Regardless of genotype and sex, the AA diet reduced femoral size, as manifested in a significant reduction in femoral cross sectional area (CSA) and in the femoral perimeter, compared with the casein and GMP diets (FIGS. 7A-7C). Femoral size expressed as the cross sectional moment of inertia (CSMI), a measure of the distribution of material around a neutral axis, was also significantly lower in PKU mice fed the AA diet compared with the casein and GMP diets (Table 6). Consequent to the reduction in femoral size, both WT and PKU mice fed an AA diet tolerated a lower maximum load compared with the GMP diet (FIG. 7D). Tissue level analysis across diet treatments provides supporting evidence that the AA diet yields a more brittle and weaker bone compared to the GMP diet in that it decreases yield strain, total strain, and maximum stress in PKU mice (Table 7). At the tissue level, both WT and PKU female mice showed significantly greater femoral weakness expressed as tolerance to a lower maximum stress before fracture when fed the AA diet compared with the GMP and casein diets (Table 7, sex x diet interaction, $p<0.0249$); this response was not observed in male mice. In summary, the reduction in both femoral size and maximum load in mice fed the low-phe AA diet suggests that providing dietary protein from GMP rather than AA attenuates the PKU bone phenotype.

Principal Components Analysis.

The bone properties we measured in this study are not mutually independent. For example, yield load and maximum load are highly correlated (Table 8). Furthermore, with so many properties measured, one might ask which are most important. PCA provides a linear transformation of the raw data to an equal number of mutually orthogonal PCs, each of which is a linear function of the raw data [31, 32]. By established convention, further analysis is limited to those PCs with Eigenvalues exceeding 1. The goal of the analysis is to explain the experimental variation while reducing the dimensionality of the data and maintaining the statistical independence of the PCs. PCA of 16 whole bone femoral measurements yielded four PCs with Eigenvalues $>1$, which collectively accounted for 87% of the variance (Table 9).

TABLE 8

Correlations among phenotypes.

| | Mass | CSA | Perim | InMin | InMaj | OutMin | OutMaj | SF | CSMI | PYD | TD | Stiff | YLoad | MLoad | Energy | fBMD |
|---|---|---|---|---|---|---|---|---|---|---|---|---|---|---|---|---|
| Mass | — | 0.45 | 0.63 | 0.30 | 0.56 | 0.29 | 0.67 | 0.61 | 0.47 | 0.27 | 0.29 | -0.15 | -0.08 | -0.10 | 0.22 | 0.14 |
| CSA | | — | 0.73 | 0.23 | 0.33 | 0.65 | 0.71 | 0.36 | 0.85 | 0.23 | 0.24 | 0.39 | 0.44 | 0.51 | 0.40 | 0.64 |
| Perim | | | — | 0.67 | 0.80 | 0.74 | 0.97 | 0.61 | 0.87 | 0.30 | 0.33 | -0.01 | 0.11 | 0.10 | 0.29 | 0.31 |
| InMin | | | | — | 0.70 | 0.78 | 0.58 | 0.09 | 0.65 | 0.10 | 0.10 | -0.07 | -0.01 | 0.01 | 0.03 | 0.06 |
| InMaj | | | | | — | 0.53 | 0.82 | 0.60 | 0.64 | 0.34 | 0.36 | -0.16 | -0.08 | -0.12 | 0.22 | 0.11 |
| OutMin | | | | | | — | 0.63 | -0.04 | 0.91 | 0.13 | 0.14 | 0.25 | 0.33 | 0.40 | 0.22 | 0.42 |
| OutMaj | | | | | | | — | 0.75 | 0.79 | 0.31 | 0.35 | -0.02 | 0.08 | 0.06 | 0.30 | 0.31 |
| SF | | | | | | | | — | 0.25 | 0.29 | 0.33 | -0.22 | -0.17 | -0.25 | 0.19 | 0.05 |
| CSMI | | | | | | | | | — | 0.26 | 0.27 | 0.28 | 0.35 | 0.42 | 0.56 | 0.53 |
| PYD | | | | | | | | | | — | 0.98 | 0.00 | -0.05 | -0.02 | 0.86 | 0.11 |
| TD | | | | | | | | | | | — | -0.10 | -0.02 | -0.05 | 0.84 | 0.09 |
| Stiff | | | | | | | | | | | | — | 0.46 | 0.73 | 0.20 | 0.68 |
| YLoad | | | | | | | | | | | | | — | 0.85 | 0.30 | 0.67 |
| MLoad | | | | | | | | | | | | | | — | 0.36 | 0.76 |

TABLE 8-continued

Correlations among phenotypes.

|  | Mass | CSA | Perim | InMin | InMaj | OutMin | OutMaj | SF | CSMI | PYD | TD | Stiff | YLoad | MLoad | Energy | fBMD |
|---|---|---|---|---|---|---|---|---|---|---|---|---|---|---|---|---|
| Energy |  |  |  |  |  |  |  |  |  |  |  |  |  |  | — | 0.39 |
| fBMD |  |  |  |  |  |  |  |  |  |  |  |  |  |  |  | — |

Phenotypes are Mass, body mass;
CSA, cortical cross-sectional area;
Perim, periosteal perimeter;
InMin, inner minor axis;
InMaj, inner major axis;
OutMin, outer minor axis;
OutMaj, outer major axis;
SF, shape factor;
CSMI, cross-sectional moment of inertia;
PYD, post-yield deflection;
TD, total deflection;
Stiff, stiffness;
YLoad, yield load;
MLoad, maximum load;
Energy, energy to failure;
fBMD, BMD by ex vivo DXA.
Each cell shows R.

TABLE 9

Principal Component Analysis.

|  | PC1 | PC2 | PC3 | PC4 |
|---|---|---|---|---|
| Eigenvalue | 6.68 | 3.57 | 2.39 | 1.29 |
| Difference | 3.11 | 1.19 | 1.09 | 0.72 |
| $r^2$ | 0.418 | 0.223 | 0.149 | 0.081 |
| Cumulative $r^2$ | 0.418 | 0.641 | 0.79 | 0.871 |

Difference is subtraction of subsequent PC from former PC.

The PCs are composites of all the measured parameters, but can be interpreted on the basis of the coefficients for each, as summarized in the Eigenvectors (Table 10). PC1 is "size-like," with cross-sectional area, perimeter, inner major axis, outer minor axis, outer major axis, and cross-sectional moment of inertia contributing most to it. PC2 is "strength-like," but at the material rather than the whole-bone level, with large contributions from stiffness, yield and maximum load, and BMD, but with negative contributions from multiple size parameters. PC3 is "ductility-like," with post-yield deflection, total deflection, and energy to failure prominent contributors. PC4 is the most difficult to interpret, with body mass, cross-sectional area, shape factor, and areal BMD of femora having large coefficients. Regardless of their interpretation, it is notable that there are significant genotype-dependent differences in all 4 PCs, indicating that the bone phenotype in PKU mice represents a global deficit in biomechanical performance (Table 11).

TABLE 10

Eigenvectors of Principal Components 1-4.

|  | PC1 | PC2 | PC3 | PC4 |
|---|---|---|---|---|
| Body mass | 0.239 | −0.205 | −0.026 | 0.318 |
| Cross-sectional area | 0.316 | 0.161 | −0.025 | 0.227 |
| Perimeter | 0.358 | −0.125 | −0.147 | 0.040 |
| Inner minor axis | 0.234 | −0.111 | −0.296 | −0.474 |
| Inner major axis | 0.289 | −0.242 | −0.116 | −0.077 |
| Outer minor axis | 0.302 | 0.107 | −0.230 | −0.375 |
| Outer major axis | 0.350 | −0.153 | −0.112 | 0.171 |
| Shape factor | 0.194 | −0.282 | 0.053 | 0.538 |
| CSMI | 0.358 | 0.081 | −0.143 | −0.122 |
| Post-yield deflection | 0.183 | −0.125 | 0.518 | −0.203 |
| Total deflection | 0.189 | −0.147 | 0.507 | −0.186 |
| Stiffness | 0.083 | 0.409 | 0.036 | 0.074 |
| Yield load | 0.123 | 0.407 | 0.028 | 0.071 |
| Max load | 0.136 | 0.468 | 0.035 | 0.027 |
| Energy | 0.209 | 0.063 | 0.506 | −0.116 |
| Femoral BMD | 0.209 | 0.362 | 0.051 | 0.202 |

CSMI, cross-sectional moment of inertia;
BMD, bone mineral density.

TABLE 11

Principal component phenotypes of WT and PKU mice fed casein, AA, and GMP diets.

| | Wild Type Mice | | | | | |
|---|---|---|---|---|---|---|
| | Males | | | Females | | |
| Variable | Casein | AA | GMP | Casein | AA | GMP |
| N | 17 | 18 | 19 | 23 | 16 | 22 |
| $_rPC1^{a,d,e}$ | 25.1 ± 0.6 | 23.4 ± 0.4 | 23.1 ± 0.6 | 24.8 ± 0.6 | 23.2 ± 0.5 | 23.9 ± 0.4 |
| $_rPC2^{a,b,e,g}$ | 40.8 ± 1.7 | 38.2 ± 1.1 | 37.0 ± 2.0 | 53.7 ± 2.4 | 46.3 ± 2.1 | 50.5 ± 1.5 |
| $_rPC3^{a,b}$ | 5.75 ± 0.23 | 5.41 ± 0.36 | 5.42 ± 0.47 | 6.58 ± 0.35 | 6.20 ± 0.20 | 6.65 ± 0.30 |
| $_rPC4^{a,b,e}$ | 17.3 ± 0.4 | 15.9 ± 0.2 | 15.6 ± 0.4 | 16.4 ± 0.4 | 15.1 ± 0.4 | 15.5 ± 0.3 |

TABLE 11-continued

Principal component phenotypes of WT and PKU mice fed casein, AA, and GMP diets.

| | PKU Mice | | | | | |
|---|---|---|---|---|---|---|
| | Males | | | Females | | |
| Variable | Casein | AA | GMP | Casein | AA | GMP |
| N | 18 | 16 | 14 | 19 | 20 | 13 |
| $^t$PC1$^{a,d,e}$ | 22.2 ± 0.5 | 22.4 ± 0.6 | 22.5 ± 0.8 | 20.7 ± 0.4 | 21.8 ± 0.3 | 21.4 ± 0.4 |
| $^t$PC2$^{a,b,e,g}$ | 36.4 ± 1.9 | 34.3 ± 1.7 | 37.4 ± 3.1 | 37.2 ± 1.1 | 43.1 ± 1.1 | 40.9 ± 1.4 |
| $^t$PC3$^{a,b}$ | 5.04 ± 0.36 | 4.47 ± 0.38 | 5.12 ± 0.53 | 4.75 ± 0.34 | 4.94 ± 0.23 | 4.93 ± 0.25 |
| $^t$PC4$^{a,b,e}$ | 14.9 ± 0.4 | 15.8 ± 0.5 | 15.3 ± 0.6 | 13.3 ± 0.3 | 14.7 ± 0.2 | 14.0 ± 0.4 |

Values are means ± SE;
N, no of mice;
PC, principal component.
$^t$Data transformed to satisfy assumptions of normality and variance.
$^a$genotype effect,
$^b$sex effect,
$^c$diet effect,
$^d$gt*sex effect,
$^e$gt*diet effect,
$^f$sex*diet effect,
$^g$gt*sex*diet effect.
PC1: WT mice fed Casein had a significant increase in their calculated PC1 values compared to WT mice fed GMP or AA. PKU mice on the three diets had significantly lower values than WT mice. Additionally, PKU males and females had lower values than WT males and females of which PKU female values were the lowest.
PC2: WT males fed GMP had reduced values compared to WT males fed casein, but were not different from WT males fed AA. There were no differences within the PKU male groups on the three diets, however PKU males fed AA had lower values than WT males fed AA or casein. There were no differences between the values within the WT females groups, however WT females fed AA were not different from PKU females fed GMP or AA, whereas WT females fed GMP or casein were significantly higher. PKU females fed casein had a significant reduction compared to PKU females fed AA, but not GMP. Additionally, WT females had higher values than WT males, and PKU females had higher values than PKU males with the exception of PKU females fed casein.
PC3: WT mice had greater values than PKU mice, and females had greater values than males.
PC4: WT mice fed casein had greater values than WT mice fed GMP or AA. PKU mice fed the three diets had a significant reduction in values compared to WT mice; however PKU mice fed AA were not different from WT mice fed GMP or AA. Male mice had greater values than female mice.

Discussion.

Success in managing the neurological manifestations of PKU by dietary phe restriction has allowed many patients to enjoy a greatly improved prognosis, spared of devastating cognitive impairment. Because of their improved function, other, more subtle deficits have become apparent [16]. Chief among these is skeletal fragility, as noted by multiple independent research groups [3, 4, 5, 6, 7, 8, 9, 10, 11]. However, since dietary phe restriction is initiated within days of birth, it has previously not been possible to distinguish whether skeletal fragility is a manifestation of PKU itself, or of its dietary treatment. The availability of an animal model of PKU, harboring an ENU-induced point mutation of the murine Pah gene allowed this uncertainty to be resolved experimentally [21].

Our data show that PKU mice have impaired bone biomechanical performance, regardless of the effects of sex or diet. The biomechanical deficit is complex, encompassing both strength and ductility. PCA reveals a genotype effect for all 4 PCs, confirming the principal findings of the whole bone biomechanics. Bone is a composite tissue composed of a protein matrix, containing primarily type 1 collagen, and precipitated mineral, containing primarily calcium and phosphate in the form of apatite [33]. The protein elements of bone matrix contribute tensile strength and ductility to the composite, while the mineral provides compressive strength and stiffness [34, 35]. These are distinct properties, both of which are needed to resist fracture. In our study, strength and ductility are reduced in PKU mice relative to WT mice. The finding that all 4 PCs of biomechanical performance differ significantly between genotypes further supports the inference that multiple aspects of bone function are impaired in the PKU mice relative to WT mice.

While our data clearly support the existence of deficits in bone strength and ductility in PKU mice, the present data are insufficient to identify the biochemical, cellular, and physiological mechanisms underlying them. The organic components of bone matrix are produced by osteoblasts and these are mineralized following secretion into the extracellular space [34, 36]. Matrix synthesis is a complex, hierarchically organized process, so that abnormalities at early stages will have cascading effects at higher levels of structure [35, 37]. Increased brittleness could arise as a consequence of a primary abnormality of type 1 collagen, its cross-linking, its assembly, abnormalities of other matrix proteins, disorganization of matrix assembly, or a combination of these [34, 38, 39]. Decreased strength reflects a quantitative deficit of mineralization, as suggested by our observation of decreased BMD in PKU mice, but changes in the composition or crystal structure could also contribute to reduced strength.

Our data also demonstrate that dietary protein source consistently affects both size and strength in WT and PKU mice. The AA diet impairs the radial growth of the femur, affecting all diaphyseal dimensions relative to casein (Table 6). The GMP and casein diets yielded larger femoral dimensions than the AA-based diet. This occurs in both WT and PKU mice, and is important because biomechanical performance at the whole bone is highly dependent on radial size [40]. Insufficient amounts of AA that are abundant in type 1 collagen, such as glutamic acid, arginine, lysine and proline, is one possible reason for this. Type 1 collagen comprises approximately 90% of the protein in bone matrix, and during skeletal growth, it is synthesized and degraded at a rapid rate. Subtle deficiency of amino acids that are abundant in collagen might therefore be manifested by reduced skeletal modeling. This possibility is attractive because it can account for reduced bone growth in mice fed the AA diet.

A second possibility, applicable only to the AA diet, is that the acid load imposes a metabolic burden that restricts skeletal modeling. We previously showed that PKU mice fed the AA diet experience metabolic stress as evidenced by an increase in food and water intake, and renal hypertrophy compared to mice fed a GMP diet [22]. Moreover, PKU mice fed the AA diet had an increase in energy expenditure not different from the elevation observed in PKU mice fed casein. The experiments reported here do not address whether these mechanisms contribute to restricted radial bone growth, but are readily testable.

The work reported here can only be compared to prior studies in limited ways. A prior experiment reported that 8 weeks of phe restriction improved bone status in PKU mice [41]. However, the technical quality of the bone characterization was inferior to our methods, and the work was conducted in a BTBR/J rather than a C57BL/6J background. The human literature includes several reports addressing the relationship between plasma phe and BMD. The data are equivocal on this point, with some showing a negative correlation [7, 9, 10] while other studies do not [3, 4, 6, 42]. A human cohort study reported that low BMD is apparent in patients with PKU from an early age and that the deficit remains stable over time [3]. However, since all subjects were prescribed low-phe AA diets, the contributions of genotype and diet could not be resolved.

Human work has primarily been cross-sectional and the bone characterization has been limited to clinical fractures, BMD, and serum markers of bone turnover[3, 4, 5, 6, 7, 8, 9, 10, 42, 43, 44, 45]. Use of a mouse model allowed us to overcome these limitations. We recently reported an increase in systemic inflammation as evidenced by significant splenomegaly and increases in inflammatory cytokines in PKU mice fed AA or casein diets; this response was normalized with the GMP diet [22]. Our observations parallel findings in human PKU. Roato et al. reported that activated T-cells, a major source of tumor necrosis factor alpha, induced spontaneous osteoclastogenesis which was associated with decreased bone status in human PKU [46].

Our experiment featured several notable strengths. Use of a uniform C57BL/6J genetic background eliminated possible confounding due to the segregation of genes other than Pah, and sample sizes were adequate to power important biomechanical endpoints [47]. The biomechanical characterization of the bones was comprehensive and used robust methods. Lastly, diets were isoenergetic allowing the animals' growth and metabolism to be characterized in detail [22].

Several limitations of our work must also be acknowledged. The C57BL/6 background is inbred, and therefore not reflective of the varied, outbred genetic backgrounds encountered in human PKU. The 3 point bending test, while robust and reproducible, produces experimental fractures in the mid-diaphysis of the femur, a site that is not generally susceptible to clinical fracture. Moreover, this is a skeletal site that is composed of cortical bone, so our data do not address the consequences of PKU on trabecular bone. Mice, because of their small size, do not have the osteonal structure characteristic of human cortical bone. The diets were only started at 3 weeks of age, when mice are weaned. This is distinct from PKU management in humans, which features dietary restriction beginning in the first week following birth. However, since long bones in mice undergo extensive linear and radial growth between weaning and young adulthood, most, if not all the femoral diaphyseal bone present at the time of testing was synthesized during the course of study.

In summary, the data reported here demonstrate that skeletal fragility is an intrinsic feature of PKU in mice. The biomechanical defects are complex, affecting both strength and ductility. In mice, an AA diet exacerbates skeletal fragility by limiting radial bone growth, which is attenuated by a GMP diet. As an AA diet is presently the standard of care, this finding suggests that there is a need to determine whether improved diets can improve bone health in patients with PKU. The mechanisms by which PKU causes bone fragility and the AA-based diet impairs radial bone growth remain unknown, illustrating the need for further work to fully define the skeletal pathophysiology of PKU and its treatment.

Example 3

A Glycomacropeptide Diet Increases Bone Mineralization and Bone Strength in Both Wild Type and PKU Female Mice Summary.

In this example, we further analyze the data collected in Example 2 and reported in Table 4 and Table 7. When the whole body bone mineral content (BMC) and bone mineral density (BMD) data from both PKU and wild type mice were disaggregated by sex and diet, but not by PKU status, the data surprisingly demonstrate that female mice fed the GMP diet demonstrated significantly greater bone mineralization, as shown by a statistically significant increase in BMC and BMD as compared to mice fed the control casein diet (sex x diet interaction, p<0.0043 and 0.0001, respectively). Consistent with greater bone mineralization, tissue level analysis indicated that femora of female mice fed the GMP diet were stronger, as shown by a statistically significant increase in maximum stress tolerated before fracture, compared to mice fed the casein or AA diets (sex x diet interaction, p<0.0249). These effects occurred regardless of the PKU status of the mice (i.e., it occurred in both wild type and PKU mice). Notably, these effects did not occur in male mice.

Materials and Methods.

The experimental design and data collection and analysis was described in detail in Example 2 (also see [48]). As noted, the experiment controlled for three main effects and their interactions in a 2×2×3 factorial design: genotype (WT or PKU), sex (male or female), and diet (low-phe GMP and low-phe AA, or high-phe casein), with the casein diet serving as a control diet. Dual-energy x-ray absorptiometry (DXA) with PIXImus software version 2.10 (GE/Lunar Corp, Madison, Wis.) was performed to obtain in vivo whole body bone mineral density (BMD) and bone mineral content (BMC) at the end of the experiment.

Tissue level analysis of biomechanical performance was performed as described in Example 1. Specifically, we tested femoral diaphysis biomechanical performance by quasi-static 3-point bending under displacement control at a rate of 0.3 mm/sec, with a support span of 7.5 mm as previously described, FIG. 5B. This produces a mid-diaphyseal fracture directly below the crosshead. By using the femoral condyles and the $3^{rd}$ trochanter as anatomical landmarks to position bones consistently, the testing protocol produces highly reproducible fractures. We obtained the periosteal perimeter, cortical cross-sectional area, outer and inner major and minor axis lengths, shape factor (ratio of outer major axis length to outer minor axis length), and cross-sectional moment of inertia in the fracture plane from digital photographs [27]. We used the geometric properties and the whole bone mechanical testing data to calculate the material properties of the bone tissue according to the standard beam theory equations [23], using the averages of both femora for further analysis: Stress ($\sigma$), (MPa)=FLc/4I with F=force, L=length, c=outer radius in the plane of bending, and I=cross-sectional moment of inertia in the plane of bending. Strain ($\epsilon$), (mm/mm)=12cd/$L^2$ with c=outer radius in the plane of bending, d=displacement, L=length. Young's Modulus (E), (MPa)=(F/d)(L³/48I), with F=force, L=length, and I=cross sectional moment of inertia in the plane of bending. Data were analyzed by three-way ANOVA to determine the effects of genotype, sex, and diet as well as their two and three way interactions.

Results.

Whole Body Bone Mineral Content and Mineral Density.

As shown in FIG. 8, female mice fed the GMP diet exhibited significantly greater bone mineralization than female mice fed the control casein diet, as shown by both increased bone mineral content and increased bone mineral density. Notably, this effect did not occur in wild type or PKU male mice, but occurred in both PKU and wild type female mice, indicating that the effect is sex based and independent of GMP's potential use as an alternative to amino acid diets among individuals with PKU. Thus, in females with or without PKU, GMP may be administered to increase the rate of bone mineralization, increase bone mineral content, or increase bone mineral density.

Tissue Level or Material Properties of Femora Reflecting Bone Strength.

As shown in FIG. 9, female mice fed the GMP diet exhibited significantly greater bone strength than female mice fed the control casein diet or the AA diet, as shown by tolerance to increased maximum stress before femoral fracture. Notably, this effect did not occur in wild type or PKU male mice, but occurred in both PKU and wild type female mice, indicating that the effect is sex based and independent of GMP's potential use as an alternative to amino acid diets among individuals with PKU. Thus, in females with or without PKU, GMP may be administered to increase bone strength as assessed by the material properties of femora.

Discussion.

Osteoporosis, characterized by decreases in skeletal bone mass, mineral density and strength, often results in bone fragility and increased susceptibility to fracture and associated morbidity. Osteoporosis is preceded by clinical osteopenia. The frequency of osteopenia and osteoporosis increases with age and is more common in women than men. Evidence suggests that the whey protein GMP shows specific benefits to female mice, both wild type and PKU, to increase whole body bone mineral content and bone mineral density, as well as femoral bone strength, compared with a control casein diet or AA diet. GMP compositions including a food product, neutraceutical or a dietary supplement may provide an effective strategy to prevent osteopenia, osteoporosis, and other conditions associated with bone mineral loss and skeletal fragility in female human or non-human animal. Bone is a composite tissue composed of a protein matrix and precipitated mineral containing primarily calcium and phosphate [33]. The protein elements of bone matrix contribute tensile strength and ductility to the composite, while the mineral provides compressive strength and stiffness [34, 35]. These are distinct properties, both of which are needed to resist fracture. In our study, both wild type and PKU female mice fed the GMP diet showed significantly greater bone mineralization as reflected in greater whole body bone mineral content and bone density compared with the control casein diet. This effect of greater whole body bone mineralization was not observed in male mice. Changes in bone mineralization due to diet were not observed with ex vivo analysis of isolated femora, although femoral strength was increased in female mice fed GMP. A reduction in bone mineralization reduces bone strength which can be assessed with the 3-point bending test. In our study we assessed the strength of femoral bones using the 3-point bending test with analysis of data at both the whole bone and tissue level. The tissue level analysis is synonymous with the material properties of bone or the performance of an idealized sample of bone tissue, independent of its size and shape [23]. Consistent with the principle of greater bone mineralization conferring greater bone strength, female mice fed the GMP diet showed greater femoral bone strength reflected in tolerance to higher maximum stress before fracture that was independent of bone size compared to the casein and AA diets. This greater bone strength was not observed in male mice and was not observed at the whole bone level possibly because of greater variance due to reduced bone size in female mice which was controlled for with the tissue level analysis. In summary, the GMP diet confers a specific benefit in both wild type and PKU female mice to increase whole body bone mineralization and increase femoral bone strength that is independent of bone size. These positive effects on bone are unique to female mice as they are not observed in male mice. GMP may provide an effective nutritional strategy to improve bone health in female human and non-human animals.

Those skilled in the art will recognize, or be able to ascertain using no more than routine experimentation, numerous equivalents to the specific materials and methods described herein. Such equivalents are considered to be within the scope of this invention and encompassed by the following claims.

References Cited in Examples 2 and 3

1. NIH (2000) Phenylketonuria (PKU): screening and management. NIH Consensus Statement 17: 1-33.
2. MacLeod E L, Ney D M (2010) Nutritional management of phenylketonuria. Ann Nestle 68: 58-69.
3. de Groot M J, Hoeksma M, van Rijn M, Slart R H, van Spronsen F J (2012) Relationships between lumbar bone mineral density and biochemical parameters in phenylketonuria patients. Mol Genet Metab 105: 566-570.
4. Perez-Duenas B, Cambra F J, Vilaseca M A, Lambruschini N, Campistol J, et al. (2002) New approach to osteopenia in phenylketonuric patients. Acta Paediatr 91: 899-904.
5. Greeves L G, Carson D J, Magee A, Patterson C C (1997) Fractures and phenylketonuria. Acta Paediatr 86: 242-244.
6. Zeman J, Bayer M, Stepan J (1999) Bone mineral density in patients with phenylketonuria. Acta Paediatr 88: 1348-1351.
7. McMurry M P, Chan G M, Leonard C O, Ernst S L (1992) Bone mineral status in children with phenylketonuria—relationship to nutritional intake and phenylalanine control. Am J Clin Nutr 55: 997-1004.
8. Allen J R, Humphries I R, Waters D L, Roberts D C, Lipson A H, et al. (1994) Decreased bone mineral density in children with phenylketonuria. Am J Clin Nutr 59: 419-422.
9. Schwahn B, Mokov E, Scheidhauer K, Lettgen B, Schonau E (1998) Decreased trabecular bone mineral density in patients with phenylketonuria measured by peripheral quantitative computed tomography. Acta Paediatr 87: 61-63.
10. Al-Qadreh A, Schulpis K H, Athanasopoulou H, Mengreli C, Skarpalezou A, et al. (1998) Bone mineral status in children with phenylketonuria under treatment. Acta Paediatr 87: 1162-1166.
11. Koura H M, Abdallah Ismail N, Kamel A F, Ahmed A M, Saad-Hussein A, et al. (2011) A long-term study of bone mineral density in patients with phenylketonuria under diet therapy. Arch Med Sci 7: 493-500.
12. Koch R, Burton B, Hoganson G, Peterson R, Rhead W, et al. (2002) Phenylketonuria in adulthood: a collaborative study. J Inherit Metab Dis 25: 333-346.

13. MacDonald A (2000) Diet and compliance in phenylketonuria. Eur J Pediatr 159 Suppl 2: S136-141.
14. Macdonald A, Daly A, Davies P, Asplin D, Hall S K, et al. (2004) Protein substitutes for PKU: what's new? J Inherit Metab Dis 27: 363-371.
15. Walter J H, White F J, Hall S K, MacDonald A, Rylance G, et al. (2002) How practical are recommendations for dietary control in phenylketonuria? Lancet 360: 55-57.
16. Enns G M, Koch R, Brumm V, Blakely E, Suter R, et al. (2010) Suboptimal outcomes in patients with PKU treated early with diet alone: revisiting the evidence. Mol Genet Metab 101: 99-109.
17. Laclair C E, Ney D M, MacLeod E L, Etzel M R (2009) Purification and use of glycomacropeptide for nutritional management of phenylketonuria. J Food Sci 74: E199-206.
18. Ney D M, Gleason S T, van Calcar S C, Macleod E L, Nelson K L, et al. (2009) Nutritional management of PKU with glycomacropeptide from cheese whey. J Inherit Metab Dis 32: 32-39.
19. Van Calcar S C, Macleod E L, Gleason S T, Etzel M R, Clayton M K, et al. (2009) Improved nutritional management of phenylketonuria by using a diet containing glycomacropeptide compared with amino acids. Am J Clin Nutr 89: 1068-1077.
20. Van Calcar S C and (2012) Food Products Made with Glycomacropeptide, a Low-Phenylalanine Whey Protein, Provide a New Alternative to Amino Acid-Based Medical Foods for Nutrition Management of Phenylketonuria Journal of the Academy of Nutrition and Dietetics In press.
21. McDonald J D, Bode V C, Dove W F, Shedlovsky A (1990) Pahhph-5: a mouse mutant deficient in phenylalanine hydroxylase. Proc Natl Acad Sci USA 87: 1965-1967.
22. Solverson P, Murali S G, Brinkman A S, Nelson D W, Clayton M K, et al. (2012) Glycomacropeptide, a low-phenylalanine protein isolated from cheese whey, supports growth and attenuates metabolic stress in the murine model of phenylketonuria. Am J Physiol Endocrinol Metab 302: E885-895.
23. Turner C H, Burr D B (1993) Basic biomechanical measurements of bone: a tutorial. Bone 14: 595-608.
24. Harding C O, Gillingham M B, Hamman K, Clark H, Goebel-Daghighi E, et al. (2006) Complete correction of hyperphenylalaninemia following liver-directed, recombinant AAV2/8 vector-mediated gene therapy in murine phenylketonuria. Gene Ther 13: 457-462.
25. Rogers Q R, Harper A E (1965) Amino acid diets and maximal growth in the rat. J Nutr 87: 267-273.
26. Lopez Franco G E, O'Neil T K, Litscher S J, Urban-Piette M, Blank R D (2004) Accuracy and precision of PIXImus densitometry for ex vivo mouse long bones: comparison of technique and software version. J Clin Densitom 7: 326-333.
27. Saless N, Litscher S J, Lopez Franco G E, Houlihan M J, Sudhakaran S, et al. (2009) Quantitative trait loci for biomechanical performance and femoral geometry in an intercross of recombinant congenic mice: restriction of the Bmd7 candidate interval. Faseb J 23: 2142-2154.
28. Becker R A, Chambers J M, Wilks A R (1988) The New S Language. Monterey, Calif.: Wadsworth and Brooks/Cole Advanced Books & Software. 702 p.
29. Mardia K V, Kent J T, Bibby J M (1979) Multivariate Analysis. London: Academic Press. 521 P.
30. Venables W N, Ripley B D (2002) Modern Applied Statistics with S. New York: Springer. 515 p.
31. Saless N, Litscher S J, Vanderby R, Demant P, Blank R D (2011) Linkage mapping of principal components for femoral biomechanical performance in a reciprocal HCB-8×HCB-23 intercross. Bone 48: 647-653.
32. Pearson K (1901) On lines and planes of closest fit to systems of points in space. Philos Mag 2: 559-572.
33. Frost H M (2001) From Wolff's law to the Utah paradigm: Insights about bone physiology and its clinical applications. Anatomical Record 262: 398-419.
34. Robey P G, A L B (2008) The Composition of Bone. In: CJ R, editor. Primer on the Metabolic Bone Diseases and Disorders of Bone and Mineral Metabolism. 7th ed. Washington, D.C.: American Society for Bone and Mineral Research. pp. 32-38.
35. Fratzl P (2008) Collagen: an Introduction. In: Fratzl P, editor. Collagen: Structure and Mechanics. New York: Springer. pp. 1-13.
36. Stein G S, Lian J B (1993) Molecular mechanisms mediating proliferation/differentiation interrelationships during progressive development of the osteoblast phenotype. Endocr Rev 14: 424-442.
37. Lakes R (1993) Materials with Structural Hierarchy Nature 361: 311-315.
38. Blank R D, AL B (2008) Genetic Collagen Diseases. In: Fratzl P, editor. Collagen: Structure and Mechanics. New York: Springer. pp. 447-474.
39. Marini J C, Forlino A, Cabral W A, Barnes A M, San Antonio J D, et al. (2007) Consortium for osteogenesis imperfecta mutations in the helical domain of type I collagen: regions rich in lethal mutations align with collagen binding sites for integrins and proteoglycans. Hum Mutat 28: 209-221.
40. Bonadio J, Jepsen K J, Mansoura M K, Jaenisch R, Kuhn J L, et al. (1993) A murine skeletal adaptation that significantly increases cortical bone mechanical properties. Implications for human skeletal fragility. J Clin Invest 92: 1697-1705.
41. Yannicelli S, Medeiros D M (2002) Elevated plasma phenylalanine concentrations may adversely affect bone status of phenylketonuric mice. J Inherit Metab Dis 25: 347-361.
42. Modan-Moses D, Vered I, Schwartz G, Anikster Y, Abraham S, et al. (2007) Peak bone mass in patients with phenylketonuria. J Inherit Metab Dis 30: 202-208.
43. Ambroszkiewicz J, Gajewska J, Laskowska-Klita T (2004) A study of bone turnover markers in prepubertal children with phenylketonuria. Eur J Pediatr 163: 177-178.
44. Millet P, Vilaseca M A, Valls C, Perez-Duenas B, Artuch R, et al. (2005) Is deoxypyridinoline a good resorption marker to detect osteopenia in phenylketonuria? Clin Biochem 38: 1127-1132.
45. Nagasaka H, Tsukahara H, Takatani T, Sanayama Y, Takayanagi M, et al. (2011) Cross-sectional study of bone metabolism with nutrition in adult classical phenylketonuric patients diagnosed by neonatal screening. J Bone Miner Metab 29: 737-743.
46. Roato I, Porta F, Mussa A, D'Amico L, Fiore L, et al. (2010) Bone impairment in phenylketonuria is characterized by circulating osteoclast precursors and activated T cell increase. PLoS One 5: e14167.
47. Leppanen O V, Sievanen H, Jarvinen T L (2008) Biomechanical testing in experimental bone interventions—May the power be with you. J Biomech 41: 1623-1631.
48. Solverson P, Murali S G, Litscher S J, Blank R D, Ney D M (2012) Low Bone Strength Is a Manifestation of Phenylketonuria in Mice and Is Attenuated by a Glycomacropeptide Diet. PLoS ONE 7(9): e45165. doi:10.1371/journal.pone.0045165.

We claim:

1. A method for improving the health of a female human or non-human animal comprising administering to the animal an effective amount of a composition comprising glycomacropeptide (GMP), whereby one or more of the following occurs:
   (a) the rate of fat oxidation or fat metabolism in the animal is increased; or
   (b) the percentage of body fat in the animal is reduced.

2. The method of claim 1, wherein the female animal is human.

3. The method of claim 1, wherein the composition is administered orally.

4. The method of claim 3, wherein the composition is a food product, a nutraceutical, or a dietary supplement.

5. The method of claim 1, wherein the animal does not have phenylketonuria (PKU).

6. The method of claim 1, wherein the effective amount of the composition is such that from 0.15 to 1.0 g GMP per kg of body weight is administered to the animal per day.

7. The method of claim 1, wherein the method is used to treat one or more conditions having as a symptom reduced fat metabolism and/or an increased percentage of body fat.

8. The method of claim 7, wherein the condition treated is obesity.

* * * * *